US011823776B2

United States Patent
Goltra et al.

(10) Patent No.: US 11,823,776 B2
(45) Date of Patent: Nov. 21, 2023

(54) FILTERING MEDICAL INFORMATION

(71) Applicant: MEDICOMP SYSTEMS, INC., Chantilly, VA (US)

(72) Inventors: Peter S. Goltra, Middleburg, VA (US); Edmund M. Herrold, New York, NY (US); Daniel A. Gainer, Shenandoah Junction, WV (US)

(73) Assignee: MEDICOMP SYSTEMS, INC., Chantilly, VA (US)

( * ) Notice: Subject to any disclaimer, the term of this patent is extended or adjusted under 35 U.S.C. 154(b) by 0 days.

(21) Appl. No.: 16/586,753

(22) Filed: Sep. 27, 2019

(65) Prior Publication Data
US 2020/0027537 A1 Jan. 23, 2020

Related U.S. Application Data

(63) Continuation of application No. 14/216,680, filed on Mar. 17, 2014, now Pat. No. 10,430,906.

(Continued)

(51) Int. Cl.
*G16H 10/60* (2018.01)
*G06Q 10/10* (2023.01)
(Continued)

(52) U.S. Cl.
CPC ............. *G16H 10/60* (2018.01); *G06Q 10/10* (2013.01); *G16H 40/63* (2018.01); *G16H 40/67* (2018.01); *G16H 15/00* (2018.01)

(58) Field of Classification Search
CPC ........ G16H 10/60; G16H 15/00; G16H 50/70; G16H 30/20; G16H 80/00; G16H 30/40;
(Continued)

(56) References Cited

U.S. PATENT DOCUMENTS

| 4,839,822 A | 6/1989 | Dormond et al. |
| 5,089,978 A | 2/1992 | Lipner et al. |

(Continued)

FOREIGN PATENT DOCUMENTS

| GB | 2389290 A | 12/2003 |
| WO | 0180117 A1 | 10/2001 |

(Continued)

OTHER PUBLICATIONS

Wu, M. (2003). NLM tele-education system for radiology residents interpreting mammography (Order No. 3100361). Available from ProQuest Dissertations and Theses Professional. (305311914). Retrieved from https://dialog.proquest.com/professional/docview/305311914?accountid=131444 (Year: 2003).*

(Continued)

*Primary Examiner* — Joseph D Burgess
(74) *Attorney, Agent, or Firm* — Merchant & Gould P.C.

(57) ABSTRACT

One aspect of this disclosure is directed to methods, apparatuses, and systems for filtering medical findings. Another aspect of this disclosure is directed to methods, apparatuses, and systems for displaying filtered medical findings. Yet another aspect of this disclosure is directed to methods, apparatuses, and systems for generating user interfaces for setting parameters for filtering medical findings. Another aspect of this disclosure is directed to methods, apparatuses, and systems for displaying medical findings that passed through a filter. Another aspect of this disclosure is directed to methods, apparatuses, and systems for filtering and displaying medical information related to medical findings.

5 Claims, 16 Drawing Sheets

Related U.S. Application Data

(60) Provisional application No. 61/801,338, filed on Mar. 15, 2013.

(51) Int. Cl.
*G16H 40/63* (2018.01)
*G16H 40/67* (2018.01)
*G16H 15/00* (2018.01)

(58) Field of Classification Search
CPC ........ G16H 10/20; G16H 10/40; G16H 20/10; G16H 40/63; G16H 70/40; G16H 70/60; G16H 40/20; G16H 40/67; G16H 50/20; G16H 50/30; G16H 70/00; G16H 70/20; G16H 10/00; G06F 3/0482; G06F 3/04842; G06F 3/04847; G06F 3/0484; G06Q 10/10
See application file for complete search history.

(56) References Cited

U.S. PATENT DOCUMENTS

| | | | |
|---|---|---|---|
| 5,262,943 | A | 11/1993 | Thibado et al. |
| 5,265,010 | A | 11/1993 | Evans-Paganelli et al. |
| 5,387,164 | A | 2/1995 | Brown, Jr. |
| 5,453,009 | A | 9/1995 | Feldman |
| 5,524,645 | A | 6/1996 | Wills |
| 5,823,949 | A | 10/1998 | Goltra |
| 5,924,074 | A | 7/1999 | Evans |
| 6,177,940 | B1 | 1/2001 | Bond et al. |
| 6,518,984 | B1 | 2/2003 | Maeckel et al. |
| 7,120,646 | B2 | 10/2006 | Streepy, Jr. |
| 7,233,938 | B2 | 6/2007 | Carus et al. |
| 7,379,946 | B2 | 5/2008 | Carus et al. |
| 7,447,988 | B2 | 11/2008 | Ross |
| 7,610,192 | B1 | 10/2009 | Jamieson |
| 7,624,030 | B2 | 11/2009 | Feder et al. |
| 7,668,737 | B2 | 2/2010 | Streepy, Jr. |
| 7,725,330 | B2 | 5/2010 | Rao et al. |
| 7,739,123 | B1 | 6/2010 | Rappaport |
| 8,050,938 | B1 | 11/2011 | Green, Jr. et al. |
| 8,086,468 | B2 | 12/2011 | Kim |
| 9,396,505 | B2 | 7/2016 | Herrold et al. |
| 9,865,025 | B2 | 1/2018 | Ragusa |
| 2002/0198885 | A1 | 12/2002 | Streepy, Jr. |
| 2003/0069759 | A1 | 4/2003 | Smith |
| 2003/0105638 | A1 | 6/2003 | Taira |
| 2003/0167189 | A1 | 9/2003 | Lutgen et al. |
| 2004/0078236 | A1 | 4/2004 | Stoodley et al. |
| 2004/0220831 | A1 | 11/2004 | Fabricant |
| 2005/0027564 | A1 | 2/2005 | Yantis |
| 2005/0027566 | A1 | 2/2005 | Haskell |
| 2005/0107672 | A1 | 5/2005 | Lipscher et al. |
| 2005/0108054 | A1 | 5/2005 | Gottlieb |
| 2005/0240439 | A1 | 10/2005 | Covit et al. |
| 2005/0273363 | A1 | 12/2005 | Lipscher et al. |
| 2006/0031218 | A1 | 2/2006 | Cipollone |
| 2006/0080140 | A1 | 4/2006 | Buttner et al. |
| 2006/0101055 | A1 | 5/2006 | Valdiserri et al. |
| 2006/0122865 | A1 | 6/2006 | Preiss et al. |
| 2006/0206361 | A1 | 9/2006 | Logan, Jr. |
| 2006/0212817 | A1* | 9/2006 | Paek ............ G06F 16/951 715/745 |
| 2006/0241977 | A1 | 10/2006 | Fitzgerald et al. |
| 2006/0253431 | A1 | 11/2006 | Bobick et al. |
| 2007/0088525 | A1 | 4/2007 | Fotiades et al. |
| 2007/0088559 | A1 | 4/2007 | Kim |
| 2007/0165049 | A1 | 7/2007 | Murawski et al. |
| 2007/0185390 | A1 | 8/2007 | Perkins et al. |
| 2007/0214013 | A1 | 9/2007 | Silverman |
| 2007/0244911 | A1 | 10/2007 | Dick |
| 2008/0016042 | A1 | 1/2008 | McKnight |
| 2008/0021288 | A1 | 1/2008 | Bowman et al. |
| 2008/0040161 | A1 | 2/2008 | Faux et al. |
| 2008/0046292 | A1 | 2/2008 | Myers et al. |
| 2008/0091464 | A1 | 4/2008 | Lipscher et al. |
| 2008/0208630 | A1 | 8/2008 | Fors et al. |
| 2008/0208631 | A1 | 8/2008 | Morita et al. |
| 2008/0215367 | A1 | 9/2008 | Marshall |
| 2008/0215369 | A1 | 9/2008 | Lareau |
| 2008/0216010 | A1 | 9/2008 | Lareau |
| 2008/0228529 | A1 | 9/2008 | Willson et al. |
| 2008/0288292 | A1 | 11/2008 | Bi et al. |
| 2008/0319942 | A1 | 12/2008 | Courdy et al. |
| 2009/0024411 | A1 | 1/2009 | Albro et al. |
| 2009/0054743 | A1* | 2/2009 | Stewart .................. G16H 15/00 600/301 |
| 2009/0055378 | A1 | 2/2009 | Alecu et al. |
| 2009/0119128 | A1 | 5/2009 | Fitzgerald et al. |
| 2009/0177495 | A1 | 7/2009 | Abousy et al. |
| 2009/0198514 | A1 | 8/2009 | Rhodes |
| 2009/0210450 | A1 | 8/2009 | Goltra |
| 2009/0216556 | A1 | 8/2009 | Martin et al. |
| 2009/0240522 | A1 | 9/2009 | Handal |
| 2010/0017222 | A1 | 1/2010 | Yeluri et al. |
| 2010/0088117 | A1 | 4/2010 | Belden et al. |
| 2010/0094657 | A1 | 4/2010 | Stern et al. |
| 2010/0131299 | A1 | 5/2010 | Hasan et al. |
| 2010/0131883 | A1 | 5/2010 | Linthicum et al. |
| 2010/0161354 | A1 | 6/2010 | Lim et al. |
| 2010/0179827 | A1 | 7/2010 | McCallie, Jr. et al. |
| 2010/0274584 | A1 | 10/2010 | Kim |
| 2010/0280851 | A1 | 11/2010 | Merkin |
| 2010/0305969 | A1 | 12/2010 | Bacon |
| 2010/0318549 | A1 | 12/2010 | Mayr et al. |
| 2010/0328235 | A1 | 12/2010 | Taute |
| 2011/0004628 | A1 | 1/2011 | Armstrong et al. |
| 2011/0004847 | A1* | 1/2011 | Herrold .................. G06Q 10/10 715/810 |
| 2011/0112952 | A1 | 5/2011 | Annunziata et al. |
| 2011/0137132 | A1* | 6/2011 | Gustafson ............ A61B 5/4312 600/300 |
| 2011/0191343 | A1* | 8/2011 | Heaton .................. G16Z 99/00 707/E17.046 |
| 2011/0225000 | A1 | 9/2011 | Selim |
| 2012/0060216 | A1 | 3/2012 | Chaudhri et al. |
| 2012/0101846 | A1 | 4/2012 | Gotthardt et al. |
| 2012/0110016 | A1 | 5/2012 | Phillips |
| 2012/0131507 | A1* | 5/2012 | Sparandara ............ G16Z 99/00 715/833 |
| 2012/0215559 | A1 | 8/2012 | Flanagan et al. |
| 2012/0239671 | A1 | 9/2012 | Chaudhri et al. |
| 2012/0290322 | A1 | 11/2012 | Bergman et al. |
| 2012/0290328 | A1 | 11/2012 | McCallie, Jr. et al. |
| 2013/0006653 | A1 | 1/2013 | Mills |
| 2013/0046529 | A1 | 2/2013 | Grain et al. |
| 2013/0046758 | A1 | 2/2013 | Kim et al. |
| 2013/0054678 | A1 | 2/2013 | Williams et al. |
| 2013/0254187 | A1* | 9/2013 | Sugihara ............ G16H 30/40 707/723 |
| 2014/0006013 | A1 | 1/2014 | Markatou et al. |
| 2014/0022255 | A1* | 1/2014 | Barbouche ............ G16Z 99/00 345/440 |
| 2016/0203277 | A1 | 7/2016 | Okabe et al. |
| 2016/0358281 | A1* | 12/2016 | Bowyer, II ............ G16H 10/60 |

FOREIGN PATENT DOCUMENTS

| | | |
|---|---|---|
| WO | 2004008273 A2 | 1/2004 |
| WO | WO 2004/051415 A2 | 6/2004 |

OTHER PUBLICATIONS

D. Wilson, D. O'Sullivan, E. McLoughlin and M. Bertolotto, "Case-Based Decision Support for Intelligent Patient Knowledge Management," 2006 3rd International IEEE Conference Intelligent Systems, 2006, pp. 130-135, doi: 10.1109/IS.2006.348406. (Year: 2006).*

"Google patents search", Sep. 15, 2016.
"Google patents search", May 7, 2018.
"Google patents search", Sep. 23, 2019.

(56) References Cited

OTHER PUBLICATIONS

Yan et al."The Internet Based Knowledge Acquisition and Management Method to Construct Large Scale Distributed Medical Expert Systems", 2004, 1-10 pages.
"The ICD 10 Classification of Mental and Behavioural Disorders", 1993, World Health Organization.
International Search Report and Written Opinion for PCT/US2010/038878, dated Jul. 27, 2012.
Hsu W et al: "Context-Based Electronic Health Record: Toward Patient Specific Healthcare", IEEE Transactions On Information Technology in Biomedicine, IEEE Service Center, Los Alamitos, CA, US, vol. 16, No. 2, Mar. 1, 2012, pp. 228-234.
International Search Report and Written Opinion for PCT/US2014/030504 dated Aug. 27, 2014.
Supplementary European Search Report for European Application No. 14762237.7 dated Sep. 29, 2017, 7 pages.
Non-Final Office Action for U.S. Appl. No. 13/773,520, dated Jan. 4, 2022, 23 pages.
Non-Final Office Action for U.S. Appl. No. 16/015,113, dated Dec. 10, 2021, 15 pages.
Conway, Jason D., et al. "Endoscopic electronic medical record systems." Gastrointestinal endoscopy 67.4 (2008): 590-594. (Year: 2008).

\* cited by examiner

FILTERING MEDICAL INFORMATION

CROSS-REFERENCE TO RELATED APPLICATIONS

The present application is a continuation application of U.S. application Ser. No. 14/216,680 entitled FILTERING MEDICAL INFORMATION filed Mar. 17, 2014, which claims priority to U.S. Provisional Application No. 61/801,338 entitled CAREGIVER INTERFACE FOR FILTERING MEDICAL INFORMATION filed Mar. 15, 2013, the entire disclosures of which are expressly incorporated herein by reference.

TECHNICAL FIELD

The present disclosure relates to medical information, and more particularly to filtering medical information.

BACKGROUND

When a caregiver interacts with a patient, the caregiver usually makes a record of the findings from that interaction in a patient note. For example, the caregiver might record in the patient note one or more symptoms that the patient was experiencing, the results of tests, the results of a physical examination that the caregiver performed, an assessment of the patient's condition, a plan for treatment of the patient, as well as other possible information. During the creation of the note, the caregiver may wish to search medical records for information related to the condition of the patient for which the caregiver is seeing the patient. A difficulty is that the medical records may contain voluminous amounts of information and information that is not related to the purpose of the patient's visit with the caregiver. It can be cumbersome, time consuming, and confusing to sift through all of the information. Additionally, the patient note may be stored in the patient's medical record once it is complete and the addition of this information adds even more information that the caregiver (or another caregiver) may need to review for future visits.

SUMMARY

One aspect of this disclosure is directed to methods, apparatuses, and systems for filtering medical findings. Another aspect of this disclosure is directed to methods, apparatuses, and systems for displaying filtered medical findings. Yet another aspect of this disclosure is directed to methods, apparatuses, and systems for generating user interfaces for setting parameters for filtering medical findings. Another aspect of this disclosure is directed to methods, apparatuses, and systems for displaying medical findings that passed through a filter. Another aspect of this disclosure is directed to methods, apparatuses, and systems for filtering and displaying medical information related to medical findings.

DETAILED DESCRIPTION

Figure 1:
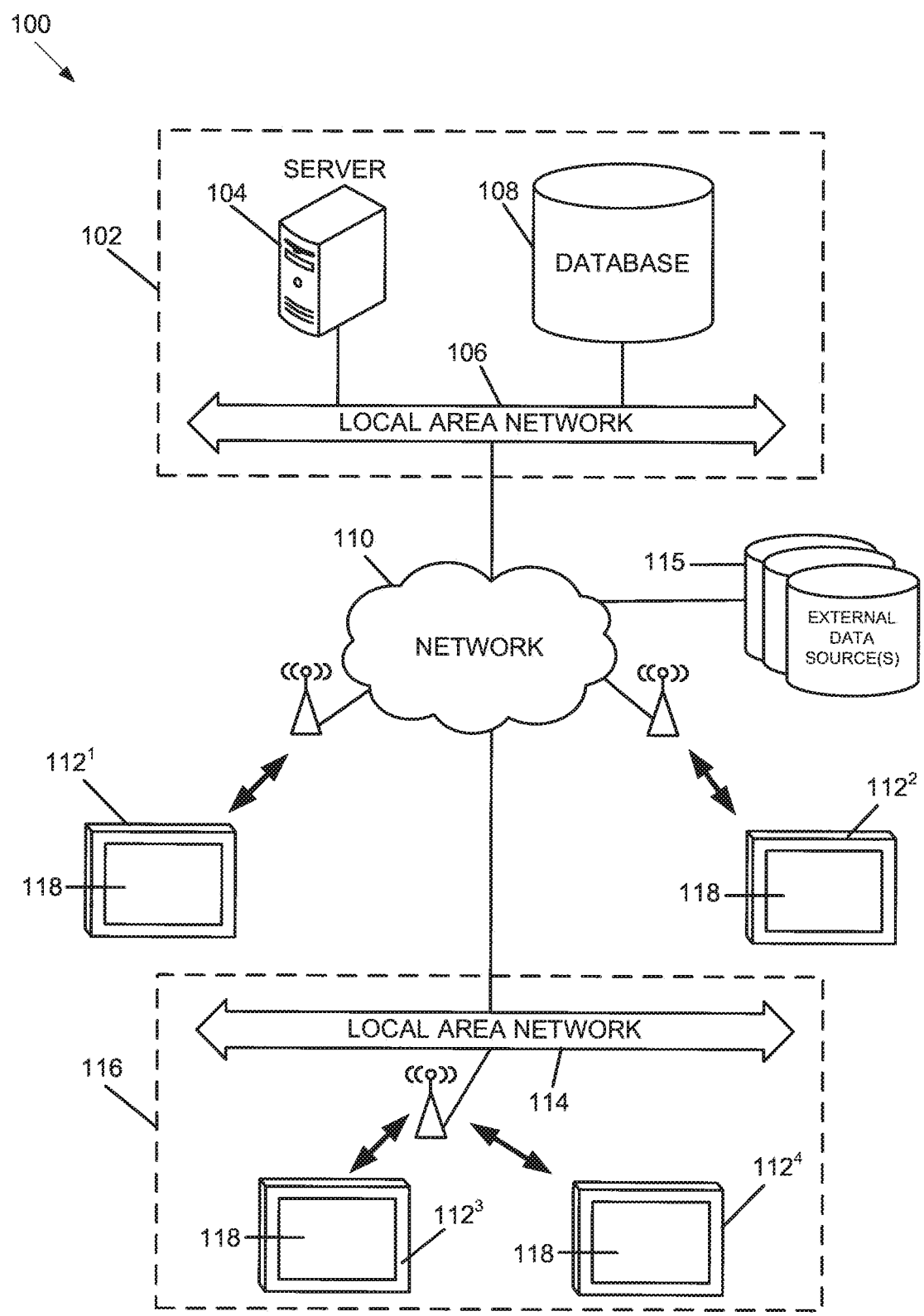
FIG. 1 is a schematic diagram illustrating an exemplary electronic medical records system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments of the appended claims.

Whenever appropriate, terms used in the singular also will include the plural and vice versa. The use of "a" herein means "one or more" unless stated otherwise or where the use of "one or more" is clearly inappropriate. The use of "or" or "and" means "and/or" unless otherwise stated or expressly implied by the context in which the word is used. The use of "comprise," "comprises," "comprising," "include," "includes," and "including" are interchangeable and not intended to be limiting. The terms "such as," "for example," "e.g.," and "i.e." also are not intended to be limiting. For example, the term "including" shall mean "including, but not limited to."

In general, the present disclosure describes systems and methods for filtering medical information or data such as findings or other related information and then presenting the filtered information to a caregiver via a graphical user interface. The graphical user interface allows caregivers to filter medical information, including medical findings from a patient's medical record or related information, to enable more effective care of the patient. At least some embodiments of the systems and methods enable a caregiver to: (i) filter the medical findings or information such as protocols based on information they enter into the system and at least some embodiments enable filtering via various filtering options; (ii) filter previously recorded patient medical records; or (iii) a combination thereof. In general, the filtering methods enable a caregiver to control the level of detail and amount of medical information that is displayed. Additionally, the system provides caregivers an opportunity to gain varying perspectives by reviewing medical information from alternate fields of medicine, for example.

Medical findings are findings that are medically-related physical or non-physical characteristics about a patient such as a medical complaint; current and past symptoms experienced by a patient; symptoms previously recorded in a patient's medical record; relevant medical history of the patient or patient's family; findings from a physical, psychological, or behavioral examination of the patient; tests performed on a patient and the results of the tests; recorded or possible diagnoses of the patient; therapy or treatment performed or prescribed; medical, psychological, and behavior conditions; procedures, medication taken or prescribed, therapies, genetic information, genetic terms, microbiome information, microbiome terms, and any other medical information related to a patient. Although the various embodiments for the systems and methods disclosed herein discuss medical findings, the systems and methods are applicable to other medical information such as various protocols that are related to a patient and the patient's findings.

The filtering methods described herein may be utilized in several electronic medical systems. For example, the systems described herein may utilize the electronic medical systems described in the patent entitled, "CAREGIVER INTERFACE FOR ELECTRONIC MEDICAL RECORDS," U.S. Pat. No. 9,396,505, issued on Jul. 19, 2016, the entire disclosure of which is incorporated by reference herein.

FIG. 1 illustrates an exemplary embodiment of an electronic medical system 100. The system 100 includes a healthcare information management system 102, a network 110, and client computing devices 112. Client computing devices 112 include stand-alone computing devices $112^1$ and $112^2$ as well as networked computing devices $112^3$ and $112^4$ that are connected to local area network 114. The electronic medical system 100 may be further connected to external data sources 115.

Some embodiments of the healthcare information management system 102 include a server 104 and a database 108 that communicate across local area network 106. The healthcare information management system 102 operates to store medical records of patients and to send selected portions of the medical records across network 110 when requested by a computing device 112. The healthcare information management system 102 can be located at the same location (such as in the same room, building, or facility) as one or more of the computing devices 112. Alternatively, the healthcare information management system 102 is located remote from the computing devices 112, such as in a different building, city, state, country, or continent.

The server 104 controls access to records and information stored in the healthcare information management system 102, including records and information stored in database 108. In at least some embodiments, the server 104 is a computing device that includes a database software application, such as the SQL SERVER® database software distributed by MICROSOFT® Corporation. In some other possible embodiments, the server 104 is a Web server or a file server. When a request for a record is received by the server 104, the server retrieves the record from the database 108 and sends it across the network 110 to the computing device 112 that requested it. Some alternative embodiments do not include a server 104, and, instead, computing devices 112 are configured or programmed to retrieve information directly from the database 108.

In at least some embodiments, the server 104 can include a single computer or device for controlling access to database 108 and can be loaded with a file server program for storing, updating, and transferring information in the database 108. In at least some alternative embodiments, the server 104 includes more than one computer. The server 104 also can run a web server for presenting the graphical user interfaces described herein to a caregiver. In these embodiments, the client computing devices 112 executes a web browser for displaying the graphical user interfaces and for enabling a caregiver to interact with the healthcare information management system 102. In at least some alternative embodiments, the computer code and functionality of the healthcare information management system 102 is divided between the server 104 and the client computing devices 112. Alternatively, the electronic medical system is stored in and executed entirely by the client computing devices 112.

The database 108 is stored on a data storage device arranged and configured to store patient medical records. Examples of storage devices for storing the database 108 include a hard disk drive, a collection of hard disk drives, digital memory (such as random access memory), a redundant array of independent disks (RAID), or other data storage devices. In at least some embodiments, records are distributed across multiple local or remote data storage devices. The database 108 stores data in an organized manner, such as in a hierarchical or relational database structure, one or more tables, or any other suitable structure useful for storing, identifying, and retrieving information. Although the database 108 is illustrated as being separated from the computing devices 112 by the network 110, the database 108 is alternatively a local data storage device of a computing device 112 or is connected to the same local area network 114 as the computing device 112.

In at least some embodiments, the healthcare information management system 102 is in data communication with or can access the external data sources 115 via the network 110. The external data sources 115, which typically include servers 104 and databases 108, may be any external supplier of medical information and/or data. For example, the external data sources 115 may be other electronic medical record systems that allow the system 100 to access patient medical records. The external data sources 115 also may be external libraries, medical terminologies, research sources, or the like, which provide the system 100 with updated medical information related to the patient's medical findings that can be provided to a caregiver for more efficient review of patient health and care for the patient.

The network 110 communicates digital data between one or more computing devices, such as between the healthcare information management system 102, the computing devices 112, and the external data sources 115. Examples of the network 110 include a local area network 114 and a wide area network, such as the Internet. The network 110 also can be a private network.

In at least some embodiments, the network 110 includes a wireless communication system, a wired communication system, or a combination of wireless and wired communication systems. A wired communication system can transmit data using electrical or optical signals in various possible embodiments. Wireless communication systems typically transmit signals via electromagnetic waves, such as in the form of radio frequency (RF) signals. A wireless communication system typically includes a RE transmitter for transmitting radio frequency signals, and an RF receiver for receiving radio frequency signals. Examples of wireless communication systems include Wi-Fi communication devices (such as utilizing wireless routers or wireless access points), cellular communication devices (such as utilizing one or more cellular base stations), and other wireless communication devices. A wireless communication system also can transmit optical signals.

In at least some embodiments, computing devices 112 are computing devices used by a caregiver and display a caregiver interface 118. The interface 118 can be generated by the caregiver's computing device 112, or they can be generated by a remote computer or server and then transmitted to the caregiver's computing device 112 for display such as a web server that generates a graphical interface and a web browser that remotely displays the graphical interface. Caregivers include physicians, psychiatrists, counselors, therapists, physician assistants, nurses, medical assistants, secretaries, receptionists, or other people that are involved in providing care to a patient. At least some embodiments also may present the user interface 118 to users that are not caregivers, but have a need to access and filter medical findings. In at least some embodiments, a computing device 112 is located at a point of care, such as within a room where a caregiver and a patient interact. A computing device 112 also can be located near the point of care, such as in a hallway or nearby room. However, in other possible embodiments, the computing device 112 is not located near the point of care.

The computing devices 112 also can be mobile computing devices that a caregiver can carry from location-to-location or from patient-to-patient. Examples of mobile computing devices include a laptop computer, an ultra-portable computer, a tablet computer (such as Tablet PC® and iPad® devices), a smartphone, or other mobile computing devices. In at least some embodiments, computing devices 112 include a touch sensitive display 156, such as shown in FIG. 2, for receiving input from a user by touching or hovering close to the display 156 with the user's finger, a stylus, or the like.

In at least some embodiments, the electronic medical system 100 includes stand-alone computing devices $112^1$ and $112^2$ and networked computing devices $112^3$ and $112^4$. Stand-alone computing devices $112^1$ and $112^2$ connect directly to network 110 and are not part of an additional local area network 114. The stand-alone computing devices $112^1$ and $112^2$ can connect to the network 110 through any suitable technology including a wireless network, such as a cellular telephone network or satellite link, cable modems, or ISDN modems. Networked computing devices $112^3$ and $112^4$ are connected to a local area network 114 which may be within a facility 116, such as a hospital, clinic, office, or other building. In at least some embodiments, a connection to the local area network 114 is made wirelessly through a wireless access point connected to the local area network 114. More or fewer computing devices 112 are included in various embodiments and can be located in one or more facilities or locations.

Figure 2:
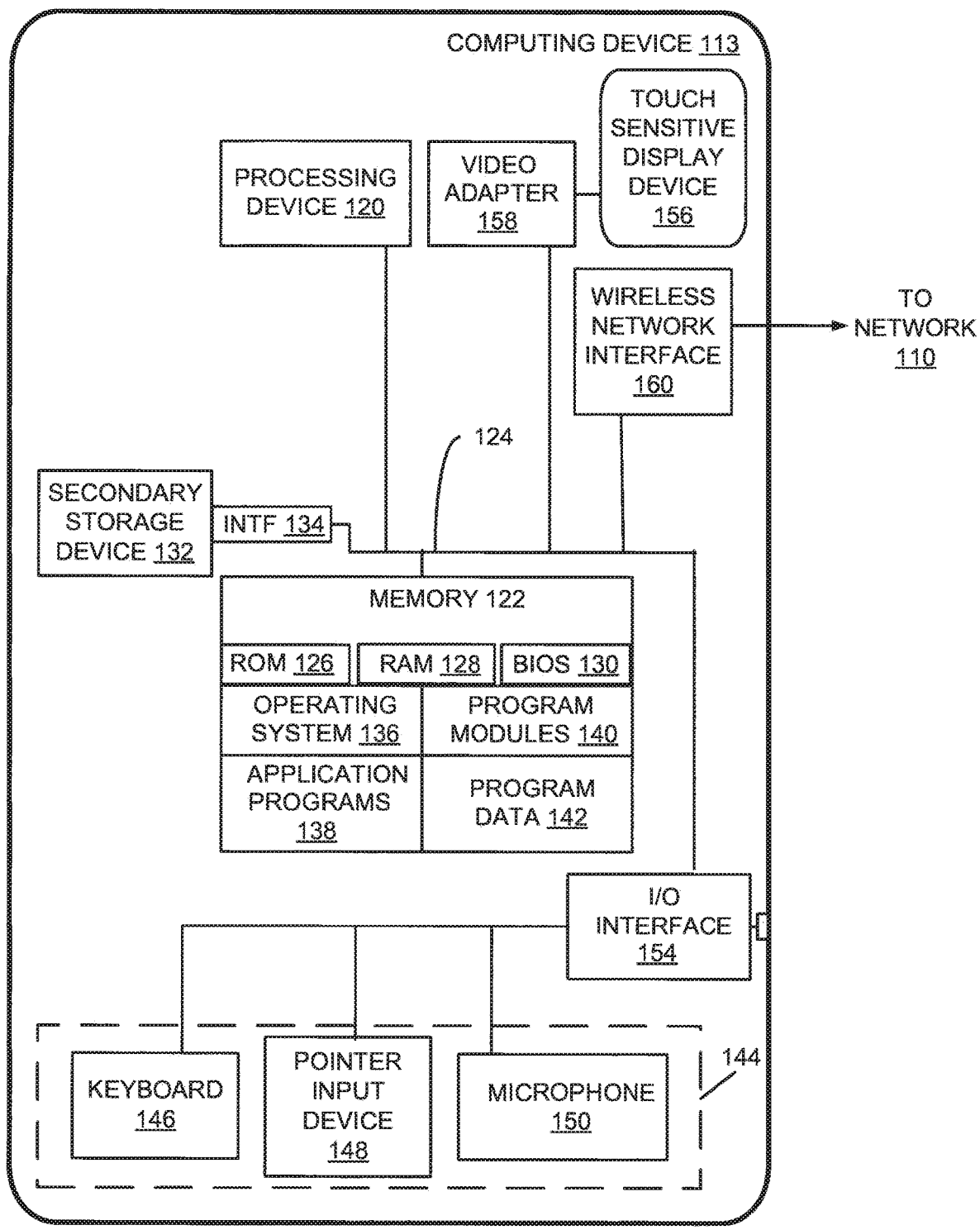
FIG. 2 is a schematic block diagram illustrating an exemplary architecture of a computing device for implementing aspects of the electronic medical system shown in FIG. 1.

FIG. 2 illustrates an exemplary architecture of a computing device 113 that can be used to implement aspects of the present disclosure, including the server 104 or the client computing device 112, and will be referred to herein as the computing device 113. The computing device 113 is used to execute the operating system, application programs, and software modules (including the software engines) described herein.

The computing device 113 includes, in at least some embodiments, at least one programmable circuit such as a processing device 120. Examples of processing devices 120 include a central processing unit (CPU) and a microprocessor. A variety of processing devices 120 are available from a variety of manufacturers, for example, Intel, Advanced Micro Devices, Qualcomm, and others. In this example, the computing device 113 also includes a system memory 122 and a system bus 124 that couples various system components including the system memory 122 to the processing device 120. The system bus 124 is one of any number of types of bus structures including a memory bus, or memory controller; a peripheral bus; and a local bus using any of a variety of bus architectures. The computing device 113 also can include a graphical processing unit separate from the processing device 120.

Examples of computing devices suitable for the computing device 113 include a desktop computer, a laptop computer, a tablet computer, a mobile phone device such as a smart phone, or other devices configured or programmed to process digital instructions.

The system memory 122 includes read only memory 126 and random access memory 128. A basic input/output system 130 containing the basic routines that act to transfer information within computing device 113, such as during start up, is typically stored in the read only memory 126.

The computing device 113 also includes a secondary storage device 132 in at least some embodiments, such as a hard disk drive, including magnetic and solid state drives, for storing digital data. The secondary storage device 132 is connected to the system bus 124 by a secondary storage interface 134. The secondary storage devices 132 and their associated computer readable media provide nonvolatile storage of computer readable instructions (including application programs and program modules), data structures, and other data for the computing device 113.

Although the exemplary environment described herein employs a hard disk drive as a secondary storage device 132, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 132 or memory 122, including an operating system 136, one or more application programs 138, other program modules 140, and program data 142.

In at least some embodiments, program data 142 includes user interface data and a word base, as described in the patent entitled, "CAREGIVER INTERFACE FOR ELECTRONIC MEDICAL RECORDS," U.S. Pat. No. 9,396,505, issued on Jul. 19, 2016, the entirety of which is incorporated by reference herein. The user interface data includes data used to generate user interfaces or that is displayed in user interfaces. Examples of user interface data includes downloaded historical records, link data, template data, and medical findings and other information for the current record. The word base includes, for example, medical vocabulary and non-medical vocabulary.

In at least some embodiments, the data stored in program data 142 can be represented in one or more files having any format usable by a computer. Examples include text files formatted according to a markup language and having data items and tags to instruct computer programs and processes how to use and present the data item. Examples of such formats include markup languages such as html, xml, and xhtml, although other formats for text files can be used. Additionally, the data can be represented using formats other than those conforming to a markup language.

In at least some embodiments disclosed herein, medical findings and other information are stored as data items in one or more data records. In at least some embodiments, data records are a set of one or more data items, such as in a format that can be read by a computing device. An example embodiment is a database record. Other examples of data records include tables, text files, computer executable files, data structures, or other structures for associating data items.

In at least some embodiments, computing device 113 includes input devices 144 to enable the caregiver to provide inputs to the computing device 113. Examples of input devices 144 include a keyboard 146, pointer input device 148, microphone 150, and touch sensitive display 156. Various embodiments also may include other input devices 144. The input devices 144 are often connected to the processing device 120 through an input/output interface 154 that is coupled to the system bus 124. These input devices 144 can be connected by any number of input/output interfaces, such as a parallel port, serial port, game port, or a universal serial bus. At least some embodiments also include wireless communication between input devices 144 and interface 154 such as infrared, BLUETOOTH® wireless technology, 802.11a/b/g/n, cellular, or other radio frequency or optical communication systems.

In this example embodiment, a touch sensitive display device 156 is also connected to the system bus 124 via an interface, such as a video adapter 158. The touch sensitive display device 156 includes touch sensors for receiving input from a user when the user touches or hovers a finger or pointer proximal to the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in at least some embodiments, converted into text inputs. It is understood that all user selections described herein may be conducted by utilizing a finger to select or move an item on the touch sensitive display device 156. The touch sensitive display device 156 can use various different technologies such as resistive, surface acoustic wave, capacitive, infrared grids, projected optical imaging, dispersive signaling, and any other suitable touch technology. User interfaces displayed on the touch sensitive display device 156 can be operated with other types of input devices 144 such as a mouse, touchpad, or keyboard. Other embodiments can use a non-touch display that is operated with an input device 144 such as a mouse, touchpad, keyboard, or other type of input device.

In addition to the display device 156, the computing device 113 can include various other peripheral devices (not shown), such as speakers or a printer.

When used in a local area networking environment or a wide area networking environment (such as the Internet), the computing device 113 is typically connected to the network 110 through a network interface, such as a wireless network interface 160. Other possible embodiments use other communication devices. For example, some embodiments of the computing device 113 include an Ethernet network interface, or a modem for communicating across the network 110.

The computing device 113 typically includes at least some form of computer-readable media. Computer readable media includes any available media that can be accessed by the computing device 113. By way of example, computer-readable media include computer readable storage media and computer readable communication media.

Computer readable storage media includes volatile and nonvolatile, removable and non-removable media implemented in any device arranged and configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 113.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, optical such as infrared, and other wireless media. Combinations of any of the above are also included within the scope of computer readable media.

Figure 3:
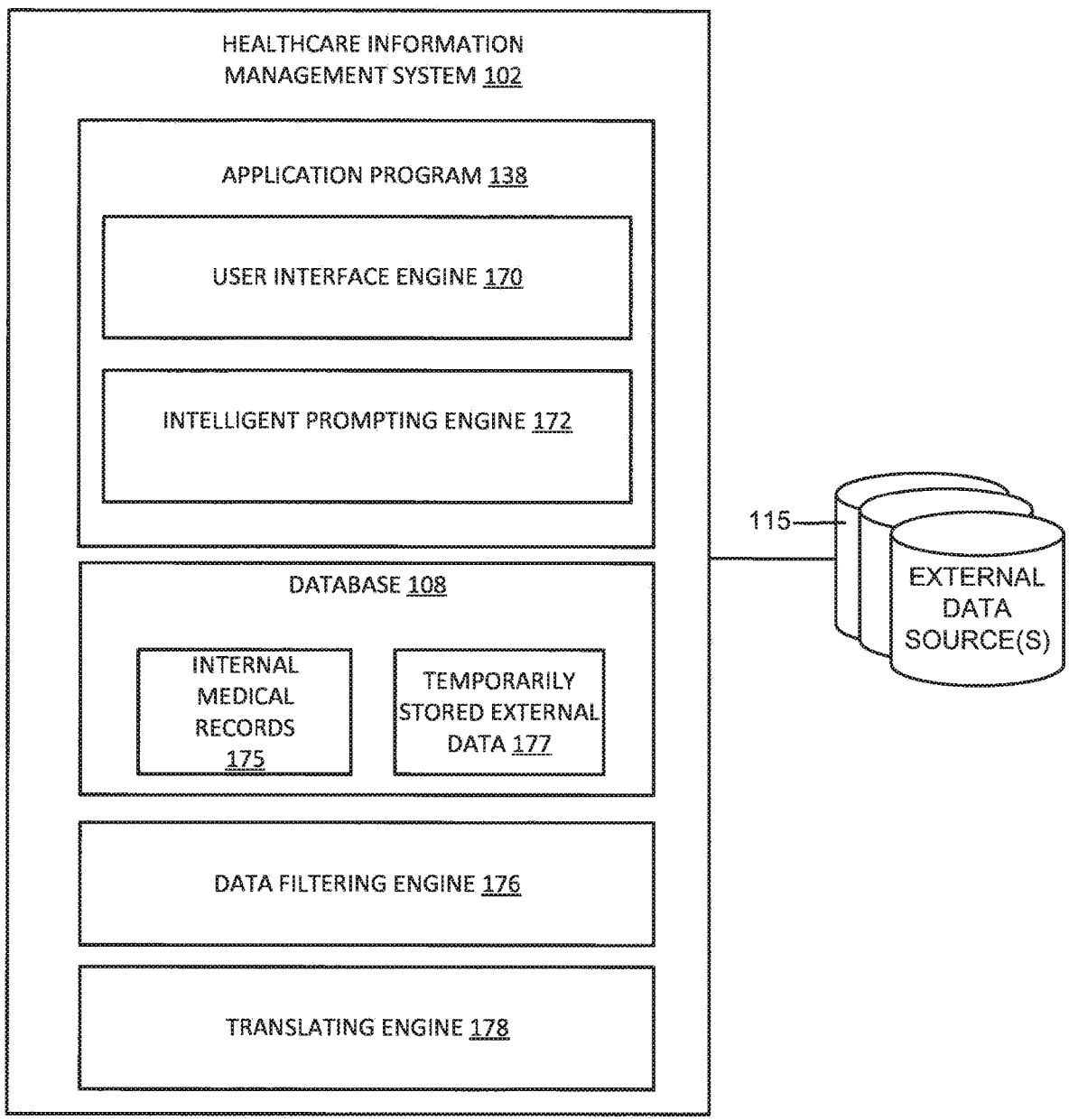
FIG. 3 is a schematic block diagram illustrating an exemplary architecture of an electronic medical system.

FIG. 3 illustrates an exemplary embodiment of the healthcare information management system 102. In this example, the system 102 includes the application program 138, the database 108, a data filtering engine 176, and a translating engine 178. The application program 138 includes a user interface engine 170 and an intelligent prompting engine 172. The database 108 includes internal medical records 175. In at least some embodiments, the database 108 also includes external data 177 that is typically temporarily stored in the database 108, although some embodiments might store the external data 177 for extended periods of time or on a more permanent bases. The healthcare information management system 102 is connected to the external data sources 115 by way of networks 110 described herein.

The database 108 is stored in one or more data storage devices, such as the memory 122 or the secondary storage device 132 (shown in FIG. 2) of the computing device 113 that forms the server 104. Alternatively, the database 108 can be stored on a memory device external to the server 104. In at least some other embodiments, the database 108 is stored in the secondary storage device 132 of the client computing device 112. Additionally, selected data can be retrieved from database 108 and stored locally on the client computing device 112.

In general, the healthcare information management system 102 allows a caregiver to review and filter medical information provided to the caregiver by the system 102. For example, the caregiver may input one or more medical findings experienced by a patient. In response to the caregiver input, the system 102 outputs on a user interface, via the user interface engine 170, a list of other medical findings associated with the medical findings experienced by the patient that are input by the caregiver. To generate this user interface, the intelligent prompting engine 172 utilizes the database 108 to determine results related to the input entered by the caregiver and generate a list of those results. The results can be determined based on a variety of factors such as known relationships between medical findings and historical symptoms or other medical findings from past patient encounters recorded in the patient's medical record. At least one possible embodiment of a system and method for intelligently prompting the caregiver based on information stored in the database 108 are discussed in detail in the patent entitled, INTELLIGENT PROMPTING, U.S. Pat. No. 5,823,949 ("the '949 patent"), issued on Oct. 20, 1998, the entire disclosure of which is hereby incorporated by reference herein. Alternative embodiments might use systems and methods other than the system and method disclosed in the '949 patent.

In at least some embodiments, the list of medical findings presented to the caregiver is quite exhaustive and includes medical findings related to several medical categories and types. For example, the results generated by the intelligent prompting engine 172 may include medical findings associated with cardiology health issues, pulmonary health issues, musculoskeletal health issues, and other health categories. Further, these results may include other medical findings without categorizing it such as symptoms, therapies, treatments, tests, or any other finding. Thus, in some instances, the caregiver may wish to narrow the search results based on one of several factors. For example, the caregiver may wish to view medical findings associated with a certain health category. By narrowing the results to a particular health category of interest, the caregiver is provided with an opportunity to more efficiently and effectively determine a health status of a patient from varying perspectives.

At least some embodiments of the system 102 allow the caregiver to sift through historical or otherwise previously recorded patient medical records. Thus, the system 102 provides caregivers an opportunity to determine a current health status of a patient by viewing select portions of medical findings from a patient's historical or otherwise previously recorded medical records. For example, patient medical records may be extensive and include medical findings from various medical categories, types, and date ranges. Thus, for the same reasons as described above, it is sometimes beneficial for a caregiver to filter a patient's medical records to identify particular medical findings which provides insight into a patient's current medical health.

In use, the data filtering engine 176 is arranged, programmed, and configured to communicate with the user interface engine 170 and the intelligent prompting engine 172. In particular, the data filtering engine 176 and the user interface engine 170 cooperate to present to the caregiver one or more options to filter results determined by the intelligent prompting engine 172 or to filter medical findings from the patient's medical records, including historical medical records. In at least some embodiments, the data filtering engine 176 utilizes filtering guidelines or parameters input by the caregiver to filter the results determined by the intelligent prompting engine 172 or medical findings from the database 108, and communicate the filtered results to the user interface engine 170 for display on a user interface.

In general, the data filtering engine 176 provides several filtering options to the caregiver. As stated above, the caregiver is provided an opportunity to filter results determined by the intelligent prompting engine 172 or filter data from the patient's medical records. The data filtering engine 176 provides filtering options, such as controlling the number of medical findings, specifying the type of medical findings, or specifying the category of medical findings.

In at least some embodiments, the data filtering engine 176 can use dates to filter medical findings. For example, the data filtering engine 176 may allow a caregiver to specify a time period during which all patient recorded symptoms or other medical findings are included as entries into the intelligent prompting engine 172. In this way, the data filtering engine 176 limits the number of medical records that are analyzed by the intelligent prompting engine 172, which in turn, filters the results presented by the intelligent prompting engine 172. A more detailed explanation of the operation of the data filtering engine 176 is described herein, including the discussion with reference to FIGS. 4-6.

The system 102 also includes the translating engine 178 which acts as an intermediary between data received from the external data sources 115 and the database 108. In some examples, data such as medical records, case studies, medical libraries, research, medical findings, and the like are received from the external data sources 115 to be used in the system 102. However, such data may enter the system in alternate formats, such as different medical terminologies and/or foreign languages. The translating engine 178 includes mapping/relationship data which it utilizes to translate data from external medical terminologies into internal medical terminologies. Examples of how the translating engine 178 may translate the information are discussed in detail in the patent application entitled "Intelligent Filtering of Health Related Information", U.S. Pat. No. 10,319,466, issued on Jun. 11, 2019, and co-pending U.S. application Ser. No. 13/773,520, entitled "Electronic Medical Coding Systems," filed on Feb. 20, 2013, the entire disclosures of both of these applications being hereby incorporated by reference. In addition, the translating engine 178 also translates data from differing foreign languages into English via an internal translator that is provided within the functionality of the translating engine 178.

Figure 4:
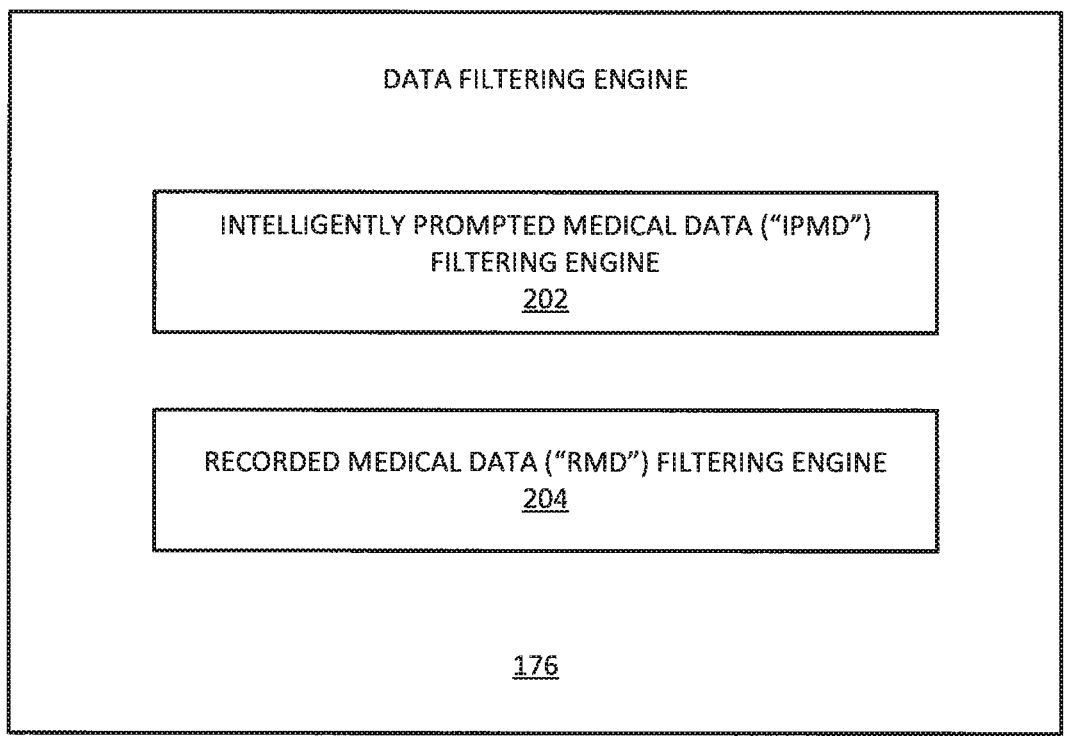
FIG. 4 is a schematic block diagram illustrating an exemplary architecture of a data filtering engine illustrated in FIG. 3.

FIG. 4 illustrates an exemplary embodiment of the data filtering engine 176. In the example, the data filtering engine 176 includes an intelligently prompted medical data ("IPMD") filtering engine 202 and a recorded medical data ("RMD") filtering engine 204. In general, the data filtering engine 176 may provide one or more methods of filtering medical findings determined by the intelligent prompting engine 172 in response to one or more caregiver-inputted entries. In addition to, or alternatively to, the data filtering engine 176 may provide one or more methods of filtering medical findings from medical records associated with a patient.

The IPMD filtering engine 202 provides the functionality to filter the results determined by the intelligent prompting engine 172. In at least some embodiments, the IPMD filtering engine 202 may filter the results in one or more ways, including, for example, by the number and type of results. In addition, the IPMD filtering engine 202 may limit the number of the patient's medical records or patient recorded encounters that are input into the system 102 to be analyzed by the intelligent prompting engine 172, thereby effectively filtering the results determined by the intelligent prompting engine 172.

For example, in at least some embodiments, the caregiver may input one or more medical findings, such as headache, cough, and fever. The intelligent prompting engine 172 may utilize these entries to determine medical findings that are associated with headache, cough, and fever. The IPMD filtering engine 202 may provide the functionality to allow the caregiver to filter the results by entering the number and/or type of results the caregiver wishes to review. For example, the caregiver may indicate that he wishes to review the top five results (e.g., five most relevant medical findings) determined by the intelligent prompting engine 172. Alternatively or additionally, the caregiver may indicate that he wishes to review only one type of medical finding. Examples of different types of medical findings include cardiology, pulmonary, infectious disease, psychiatry, oncology, etc. In at least some embodiments, the caregiver may indicate that he wishes to review more than one type of medical finding and/or indicate the percentage of a particular type of medical finding that the caregiver wishes to review.

In another example, the caregiver may select medical findings from a patient's medical history to use as parameters for filtering the medical findings the intelligent prompting engine 172 uses from the patient's medical records to determine medical findings to present to the caregiver for the current patient encounter. In yet another example, the IPMD filtering engine 202 enables the caregiver to filter medical findings input from the patient's medical record to the intelligent prompting engine 172 by a particular time period. For example, the caregiver may set the IPMD filtering engine 202 to input into the intelligent prompting engine 172 every recorded medical finding for a particular patient between the years 2010 and 2011. Thus, the intelligent prompting engine 172 would receive all recording medical findings associated with a particular patient's medical record between the years 2010 and 2011. Alternatively, the dates for filtering can be set with only a lower limit such as 2009 so that recorded medical findings from 2009 to the current patient encounter are input into the intelligent prompting engine 172. In this way, the results determined by the intelligent prompting engine 172 are filtered due to the filtering of the caregiver entries.

The recorded medical data ("PAD") filtering engine 204 provides the functionality to filter specific patient data such as medical findings from that patient's medical history. For example, the RMD filtering engine 204 enables filtering of a patient's recorded medical findings by time period, type of medical finding, or number of medical findings of a particular type. In some examples, when the caregiver identifies a number of a particular type of medical finding, the patient may have less medical findings recorded in his patient's medical record than the identified number.

Figure 5:
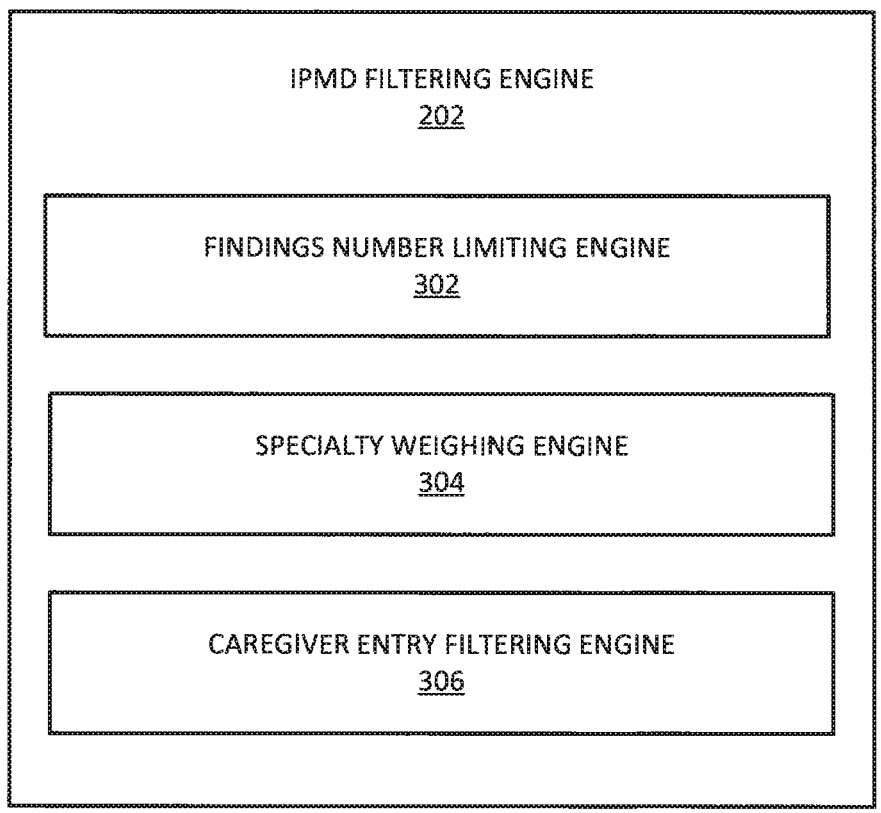
FIG. 5 is a schematic block diagram illustrating an exemplary architecture of an intelligently prompted medical data filtering engine illustrated in FIG. 3.

Now referring to FIG. 5, an exemplary embodiment of the IPMD filtering engine 202 is illustrated. In the example, the IPMD filtering engine 202 includes a findings number limiting engine 302, a specialty weighting engine 304, and a caregiver entry filtering engine 306. As explained above, in general, the IPMD filtering engine 202 provides the functionality for filtering results of the intelligent prompting engine 172.

The findings number limiting engine 302 allows a caregiver to limit the results of the intelligent prompting engine 172 to an identified number of results. For example, the caregiver may input one or more entries (e.g., medical findings) and identify the number of results he wishes to review. In at least some embodiments, the findings number limiting engine 302 may filter the results based on an internal score that indicates the level of relatedness the result is to the caregiver's one or more entries. The level of relatedness may be one or more scores indicating the relevance of the result to the one or more caregiver entries. For example, each medical finding included in the results generated by the intelligent prompting engine 172 can be assigned a score ranging from 0 to 3, with 3 being the most relevant to the medical finding from the current patient encounter, and 0 being the least relevant to the medical finding from the current patient encounter. In such embodiments, the findings number limiting engine 302 may filter the results so that the more related medical findings as determined by the intelligent prompting engine 172 are presented to the caregiver and the less related medical findings are filtered from the results of the intelligent prompting engine 172 that are displayed by the user interface engine 170. Other methods of filtering the results to retrieve the identified number of results may be utilized.

The specialty weighting engine 304 also may allow a caregiver to limit the results of the intelligent prompting engine 172 by a percentage of types of results. For example, the caregiver may indicate that of the results, he wishes to review 50% cardiology results, 25% pulmonary results, and 25% infectious disease results. In other embodiments, the caregiver may only indicate that he wishes to review 50% cardiology results, and the specialty weighting engine 304 alters the remaining percentages based on the caregiver's first percentage selection. For example, as a particular specialty percentage is decreased, one or more other specialty percentages may be increased. Similarly, as a particular specialty percentage is increased, one or more other specialty percentages may be decreased. In at least some embodiments, the database 108 includes a listing of all medical findings and one or more specialty codes associated with the medical findings. The specialty weighting engine 304 may communicate with the database 108 to retrieve the identified percentage of items in the identified specialties to present to the caregiver.

The caregiver entry filtering engine 306 also may communicate with the database 108 to retrieve patient medical histories as caregiver entries to the intelligent prompting engine 172. For example, the caregiver entry filtering engine 306 may enable the caregiver to limit a particular patient's medical history to an identified time period, such as, for example, between the years 2010 and 2011 or from 2009 to the current patient encounter. In at least some embodiments, the caregiver entry filtering engine 306 allows the caregiver to input an identified time period from as little as a few hours to as long as the patient's entire medical history from birth. The caregiver entry filtering engine 306 utilizes the inputted time period and extracts each recorded medical finding in the patient's medical history during the identified time period. The caregiver entry filtering engine 306 may feed the medical findings from the extracted medical records to the intelligent prompting engine 172 as inputs, thereby limiting the results determined by the intelligent prompting engine 172.

Figure 6:
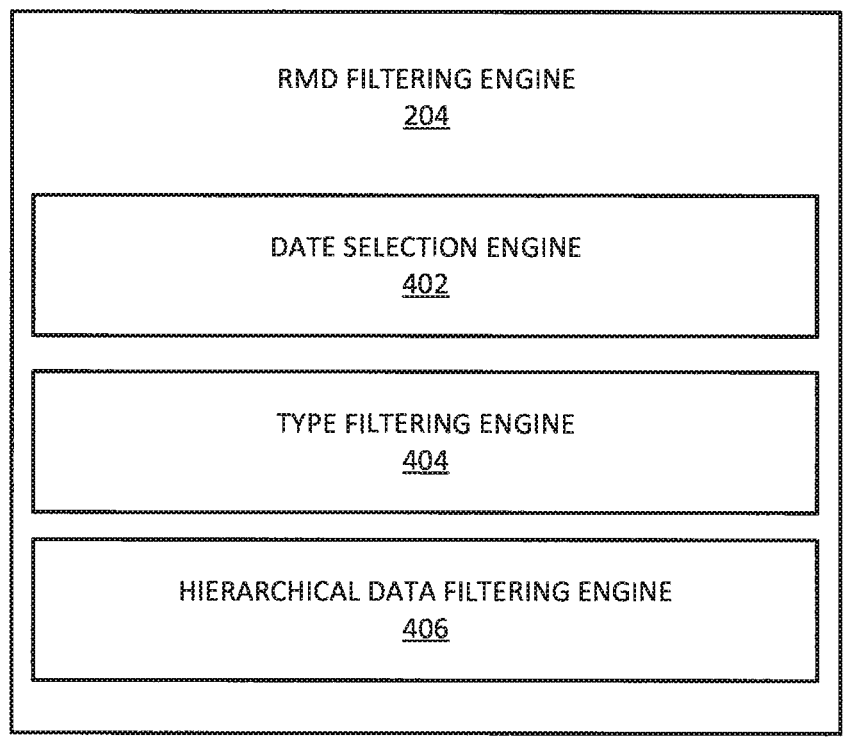
FIG. 6 is a schematic block diagram illustrating an exemplary architecture of a recorded data filtering engine illustrated in FIG. 3.

FIG. 6 is an exemplary embodiment of the RMD filtering engine 204. In the example, the RMD filtering engine 204 includes a date selection engine 402, a type filtering engine 404, and a hierarchical filtering engine 406. In general, as stated above, the RAID filtering engine 204 provides the functionality to filter a particular patient's medical history. In general, each component engine of the RMD filtering engine 204 communicates with the database 108 to access and filter patient medical records based on caregiver inputted filter guidelines or parameters.

The date selection engine 402 may enable the caregiver to filter a particular patient's medical history by specifying a particular time period. For example, the caregiver may input a particular time period ranging from as small as a few hours to as large as a patient's entire lifetime as described herein. The type filtering engine 404 may enable the caregiver to filter a particular patient's medical history by specifying a particular type of medical finding. For example, the caregiver may indicate one or more types of medical findings he wishes to review from a particular patient's medical records. In other embodiments, the caregiver may set the number of medical findings for a particular type or types of findings he wishes to review from a particular patient's medical records.

The hierarchical filtering engine 406 provides the functionality to enable the caregiver to indicate a number of medical findings having a particular form or particular forms from the patient's medical records that the caregiver wishes to review. For example, a form may include symptoms, history, physical findings, tests, and other medical findings, and the like. The caregiver may further indicate a specific time frame, as discussed above with relation to the date selection engine 402. Thereafter, the caregiver may further indicate the form and/or the number of medical findings of a particular form or forms he wishes to review from that particular time frame of the patient's medical records. In at least some embodiments, the particular number of medical findings having the forms of data the caregiver selects is not present in the patient's medical record. In these instances, the system utilizes the database 108 to extract medical findings closely related to those found in the patient's medical record. For example, the health care information management system 102 may extract medical findings that are a narrower or broader variation of the medical findings that are found in the patient's medical record. For example, if the caregiver requests two medical findings, but the patient only has one finding of "pneumonia" in his medical record, the system 102 would extract findings from the database 108 which are closely related (e.g., within the same medical family) to pneumonia, such as, for example, "aspiration pneumonia."

Figure 7:
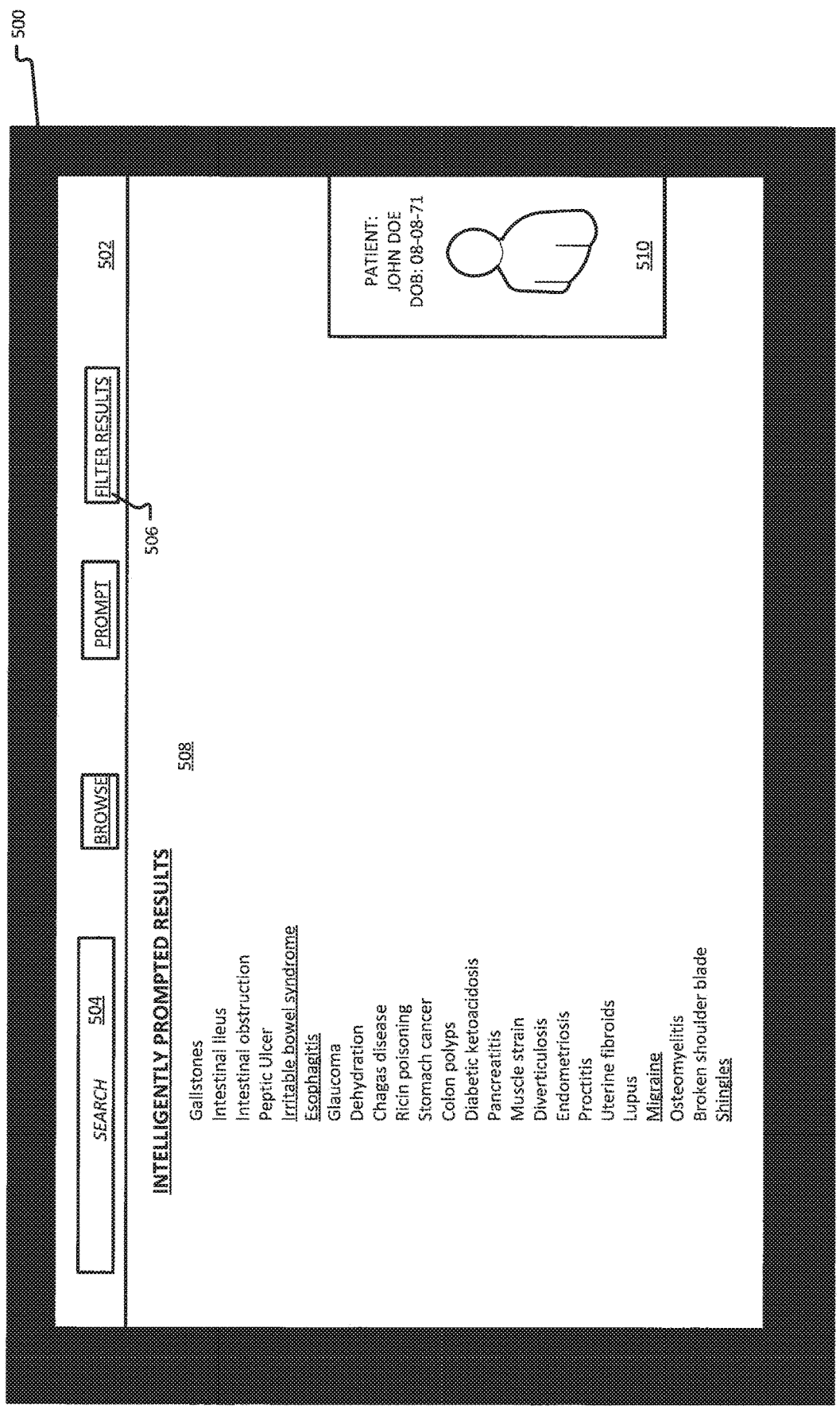
FIG. 7 is an exemplary embodiment of a caregiver user interface generated by the systems illustrated in FIGS. 1-3.

Referring now to FIG. 7, an exemplary embodiment of a graphical user interface (GUI) 500 is shown. The GUI 500 is an example of an intelligently prompted results user interface presented to a caregiver based on one or more inputs entered by the caregiver. In the example, the GUI 500 includes a header 502, a listing of results 508 generated by the intelligent prompting engine 172, and a patient summary 510. The header 502 includes a search bar 504 and a filtering option 506.

In general, the graphical user interface 500 presents the listing of results 508 to the caregiver based on entries that the caregiver previously inputted into the system. For example, to arrive at the GUI 500, the caregiver may have entered one or more medical findings presently being experienced by John Doe into the search bar 504, such as, for example, "abdominal pain, bleeding, and nausea." The listing of results 508 is a list of other medical findings related to the caregiver's entries that are somehow associated with the caregiver's entries. Thus, in at least some embodiments, the user may utilize the GUI 500 to review potential diagnoses and other medical findings that may be potentially relevant to John Doe's current status. Based on the caregiver's determination, the caregiver may select one or more of the medical findings in the listing of results 508 to gain more information (e.g., symptoms, treatments, therapies, studies, research, and the like) on that finding or to include it in the medical records of John Doe. Findings on the listing of results 508 that are underlined or otherwise highlighted may indicate that such medical findings exists in the medical record of John Doe. In at least some embodiments, the underlined findings may include a control or link such that clicking on an underlined medical findings will redirect the caregiver to that entry in the patient's medical records.

In at least some embodiments, the header 502 includes the filtering option 506. The filtering option 506 may provide the caregiver with one or more filtering options based on what is presently being viewed on the GUI 500. For example, because the listing of results 508 is a list of results determined by the intelligent prompting engine 172, the filtering option 506 may allow the caregiver to filter the results via the options discussed herein with respect to the IPMD filtering engine 202. However, in other embodiments, if recorded medical findings are being presented to the caregiver, the filtering option 506 may allow the caregiver to filter the findings via the options discussed above with respect to the RMD filtering engine 204.

Figure 8:
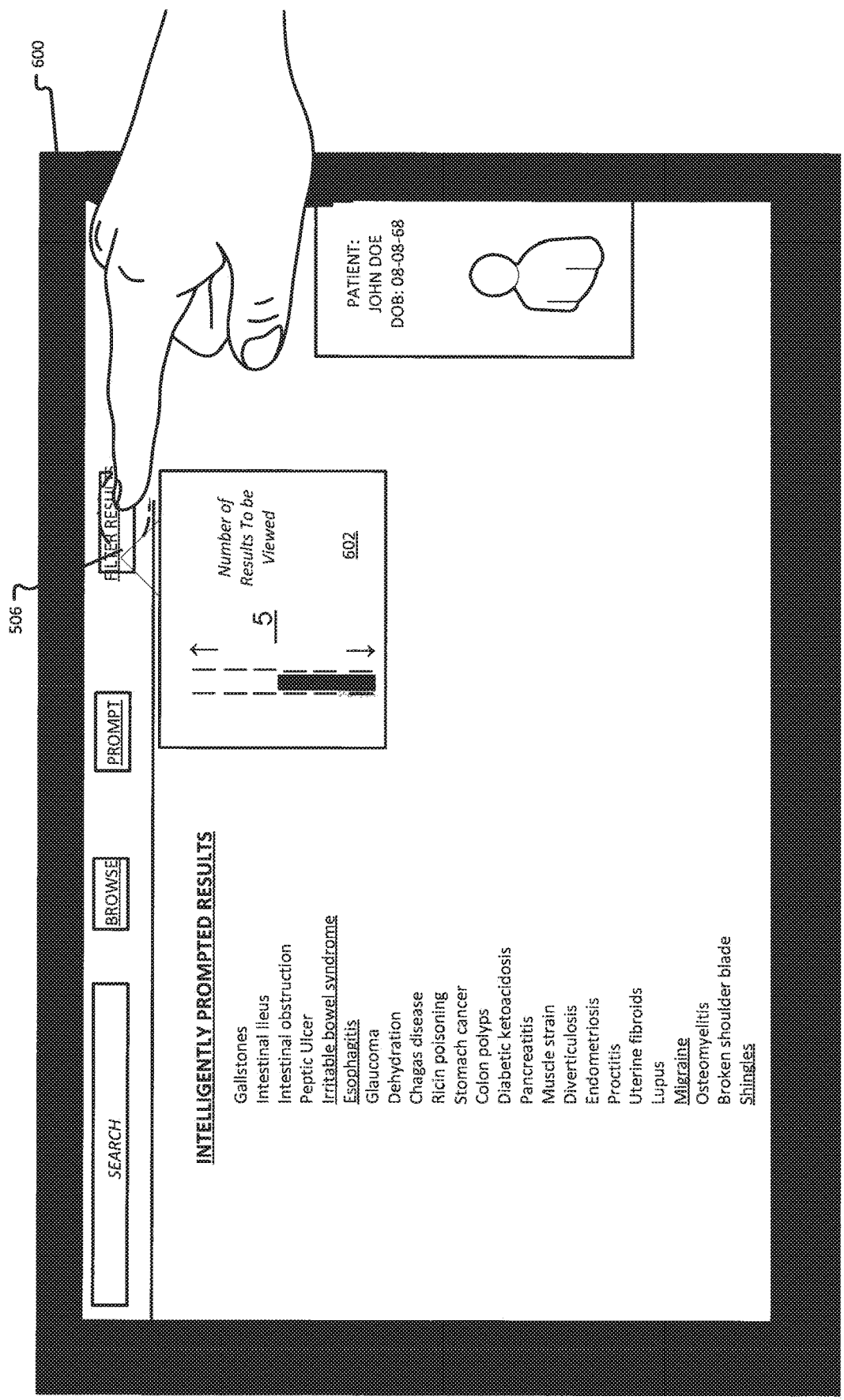
FIG. 8 is an exemplary embodiment of a caregiver user interface generated by the systems illustrated in FIGS. 1-3.

Now referring to FIG. 8, an exemplary embodiment of a graphical user interface (GUI) 600 is shown. The GUI 600 is an example of what is shown to the caregiver upon selecting the filtering option 506 of the GUI 500. The GUI 600 includes a filtering box 602.

In at least some embodiments, the caregiver may be presented with the filtering box 602 upon selecting the filtering option 506. The caregiver may select the filtering option 506 by tapping or hovering over the filtering option 506 with a finger or other input device as shown in FIG. 8. In other embodiments, the computing device 112 displaying the GUIs 500, 600 is not a touch screen device, and thus, the caregiver may utilize any input device to select the filtering option 506, including, for example, a keyboard or pointer such as a mouse. The caregiver may utilize the input device to select, right click, left click, double click, or the like, the filtering option 506.

The filtering box 602 is an example of a filtering method that may be presented to the caregiver. The filtering box 602 enables the caregiver to filter the listing of results 508 by selecting a number of results to be viewed. In the example, the caregiver may utilize a finger to slide a sliding bar in the filtering box 602 to a particular level. In at least some embodiments, the caregiver may utilize two fingers to stretch or shrink the sliding bar until a number next to the sliding bar indicates a desired number of results to be viewed. In other embodiments, the caregiver may utilize any input device to slide the sliding bar in the filtering box 602 to a particular level to indicate a desired number of results. In yet further embodiments, the filtering box 602 may not include a sliding bar, and instead include a spin wheel having possible filtering parameters or a data field for manually inputting a desired number of results to be viewed.

Figure 9:
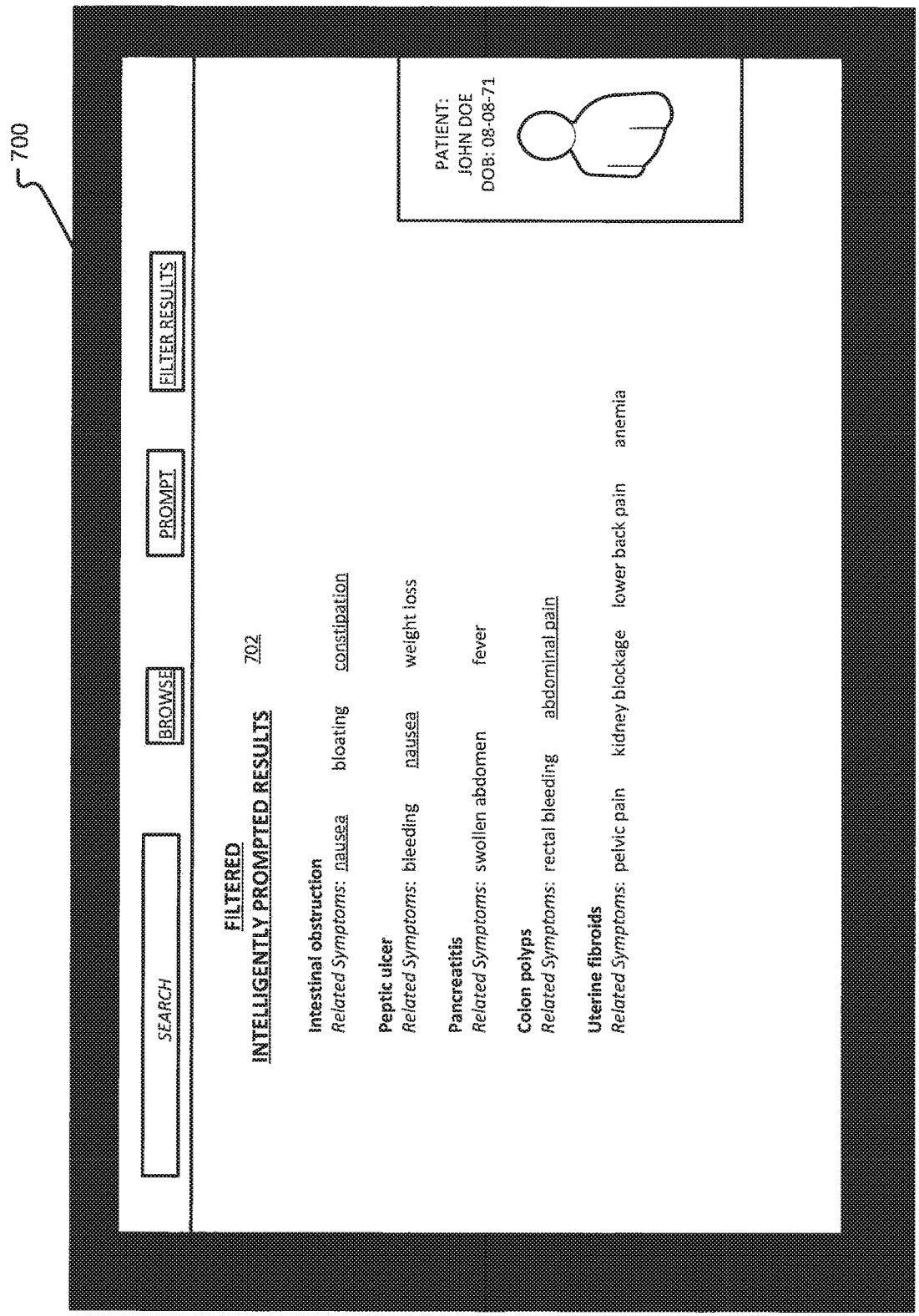
FIG. 9 is an exemplary embodiment of a caregiver user interface generated by the systems illustrated in FIGS. 1-3.

Now referring to FIG. 9, an exemplary embodiment of a GUI 700 is shown. In general, the GUI 700 is an example of a user interface and information is presented to the caregiver after the caregiver has utilized the filtering box 602 to indicate the desired number of results generated by the intelligent prompting engine 172 to be viewed. In the example, the GUI 700 includes a filtered listing of results 702 from the intelligent prompting engine 172.

The filtered listing of results 702 is a modified version of the listing of results 508 based on the desired number of results to be viewed set by the caregiver via the filtering box 602. The filtered listing of results 702 is an example of possible outputs of the findings number limiting engine 302. In at least some embodiments, the system 102 selects the findings included in the filtered listing of results 702 by utilizing a relevance score associated with each finding included in the listing of results 508. In at least some embodiments, the items with the highest relevance scores are presented to the caregiver. For example, if the caregiver selects five results in the filtering box 602, the filtered listing of results 702 include the five findings having the highest relevance score, although in alternative embodiments, the five findings to be displayed can be determined using other criteria. In alternative embodiments, the filtering box 602 enables the caregiver to select a minimum relevance score and then the filtered listing of results 702 will include those findings having a relevance score equal to or greater than the minimum relevance score.

In some situations, there may be fewer items in the listing of results 508 than the caregiver's desired number of results. When this situation occurs in at least some embodiments, the system 102 may utilize the intelligent prompting engine 172 to select more items to be presented in the filtered listing of results 702 so that the filtered listing of results 702 includes the number of findings set by the caregiver. Thus, there are some examples in which the filtered listing of results 702 includes more items than the listing of results 508. In alternative embodiments, whenever there are fewer findings in the listing of results 508 than the desired number of results as set by the caregiver in the various filters for either IPMD filtering engine 202 or the RMD filtering engine 204, the healthcare information management system 102 displays only those findings from the filtered listing of results 702 and does not add any findings or other information to the list of findings displayed by the system.

Figure 10:
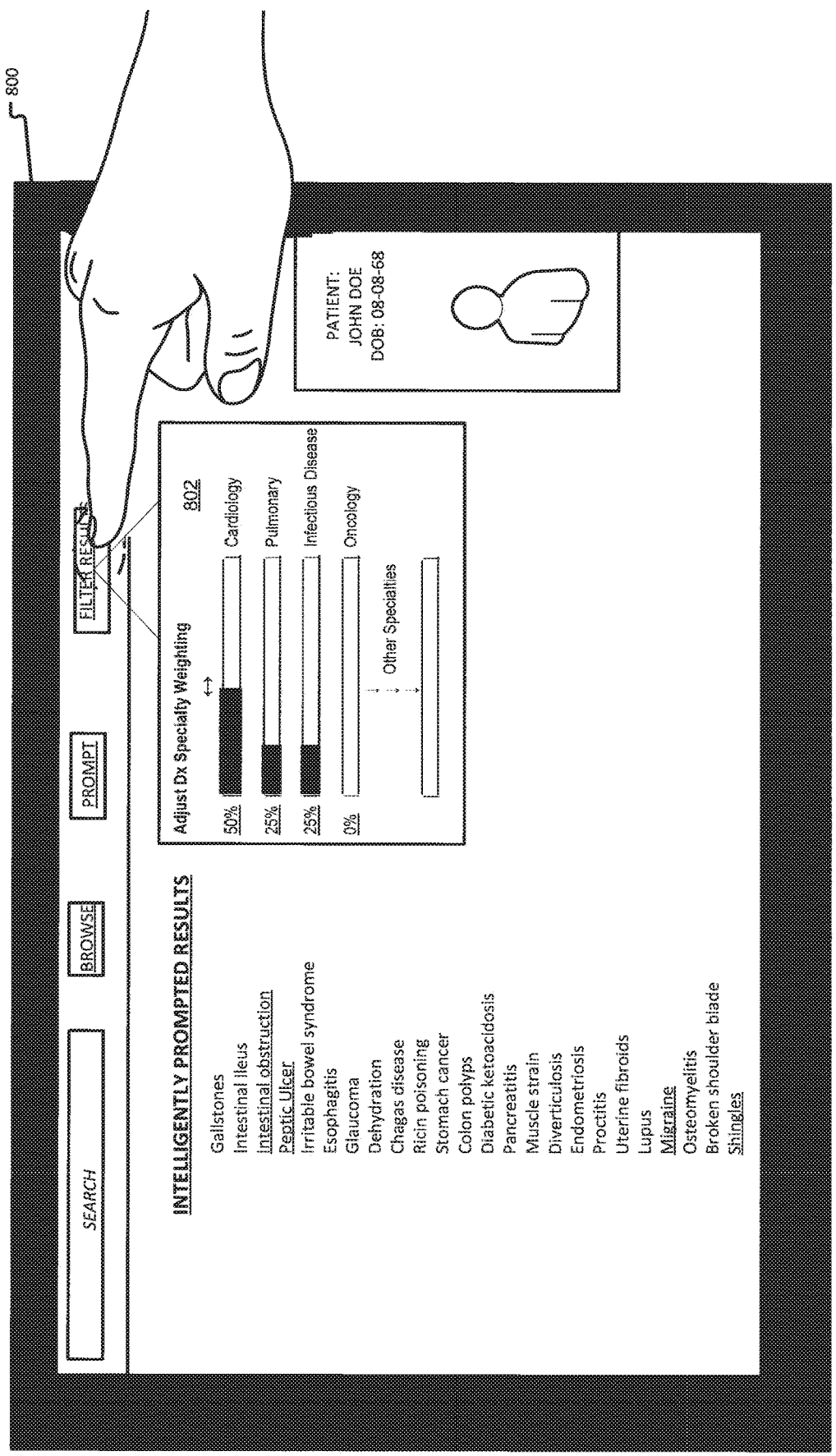
FIG. 10 is an exemplary embodiment of a caregiver user interface generated by the systems illustrated in FIGS. 1-3.

Now referring to FIG. 10, an exemplary embodiment of a GUI 800 is shown. The GUI 800 is another example of what is shown to the caregiver upon selecting the filtering option 506 of the GUI 500. In the example, the GUI 800 includes a specialty weighting filtering box 802.

The specialty weighting filtering box 802 allows the caregiver to indicate the types of results from the intelligent prompting engine 172 he wishes to review. In particular, the specialty weighting filtering box 802 allows the caregiver to indicate a percentage of each type of result he wishes to review as discussed in more detail herein. For example, the caregiver may wish to view more cardiology results than oncology results, having already determined that oncology is not a primary concern with John Doe. Thus, the caregiver may utilize the specialty weighting filtering box 802 to move the slideable bars to indicate a desired percentage of each category of items. In alternative embodiments, the caregiver can use a spin wheel, data field, or other interface for entering a desired percentage.

In at least some embodiments, as the caregiver moves one of the slideable bars to a desired percentage, the other slideable bars are automatically moved to compensate for the remaining percentage so that the total values of percentages distributed among the selected types of medical findings totals 100%. For example, as the cardiology bar is increased in percentage, the system 102 may automatically move the pulmonary bar to decrease in percentage.

As stated above, in at least some embodiments, the caregiver may move the slideable bars in the filtering box 802 with a finger or other input device. In other embodiments, the caregiver may utilize any input device, including, for example, a keyboard or pointing device such as a mouse. The caregiver may utilize the input device to select, right click, left click, double click, or the like, the filtering option 506.

Figure 11:
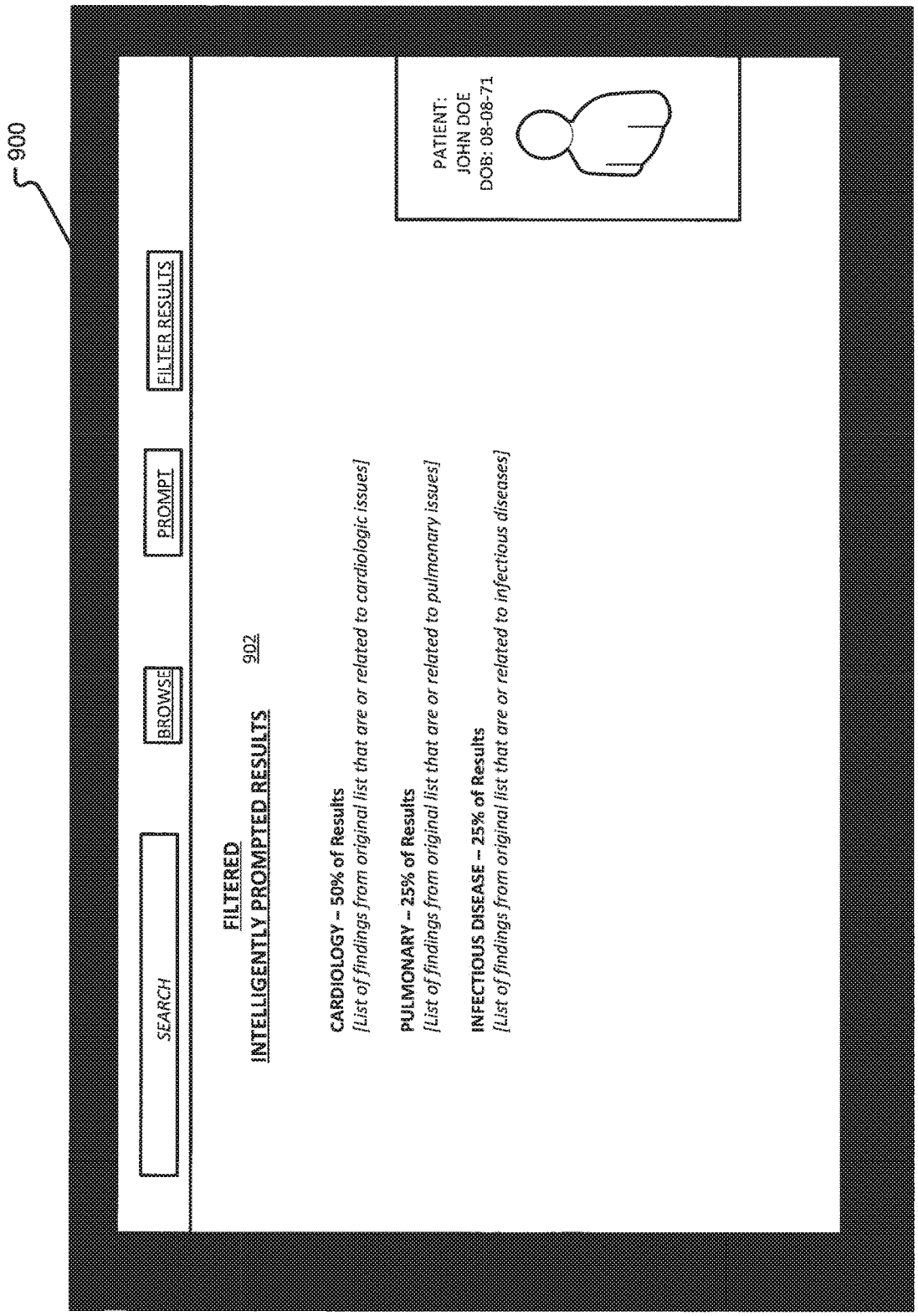
FIG. 11 is an exemplary embodiment of a caregiver user interface generated by the systems illustrated in FIGS. 1-3.

Now referring to FIG. 11, an exemplary embodiment of a GUI 900 is shown. In general, the GUI 900 is an example of what is presented to the caregiver after the caregiver has utilized the specialty weighting filtering box 802 to indicate the desired percentages of the types of findings from the results to be viewed. In the example, the GUI 900 includes a filtered listing of results 902.

In the example, the filtered listing of results 902 is an example of an output of the specialty weighting engine 304. In at least some embodiments, the specialty weighting engine 304 utilizes the caregiver inputted percentages and determines a filtered listing of results 902 by utilizing relevance scores, as discussed herein in more detail, associated with each item of the listing of results 508. The specialty weighting engine 304 may keep items with a higher relevance score over other items with lower relevance scores.

In at least some embodiments, the caregiver may request a desired percentage for one or more categories that exceeds the amount of items originally presented in the listing of results 508. In such embodiments, the intelligent prompting engine 172 may determine more items to be presented in the filtered listing of results 902 that were not present in the listing of results 508. Thus, there may be instances in which the filtered listing of results 902 is greater than the listing of results 508.

Figure 12:
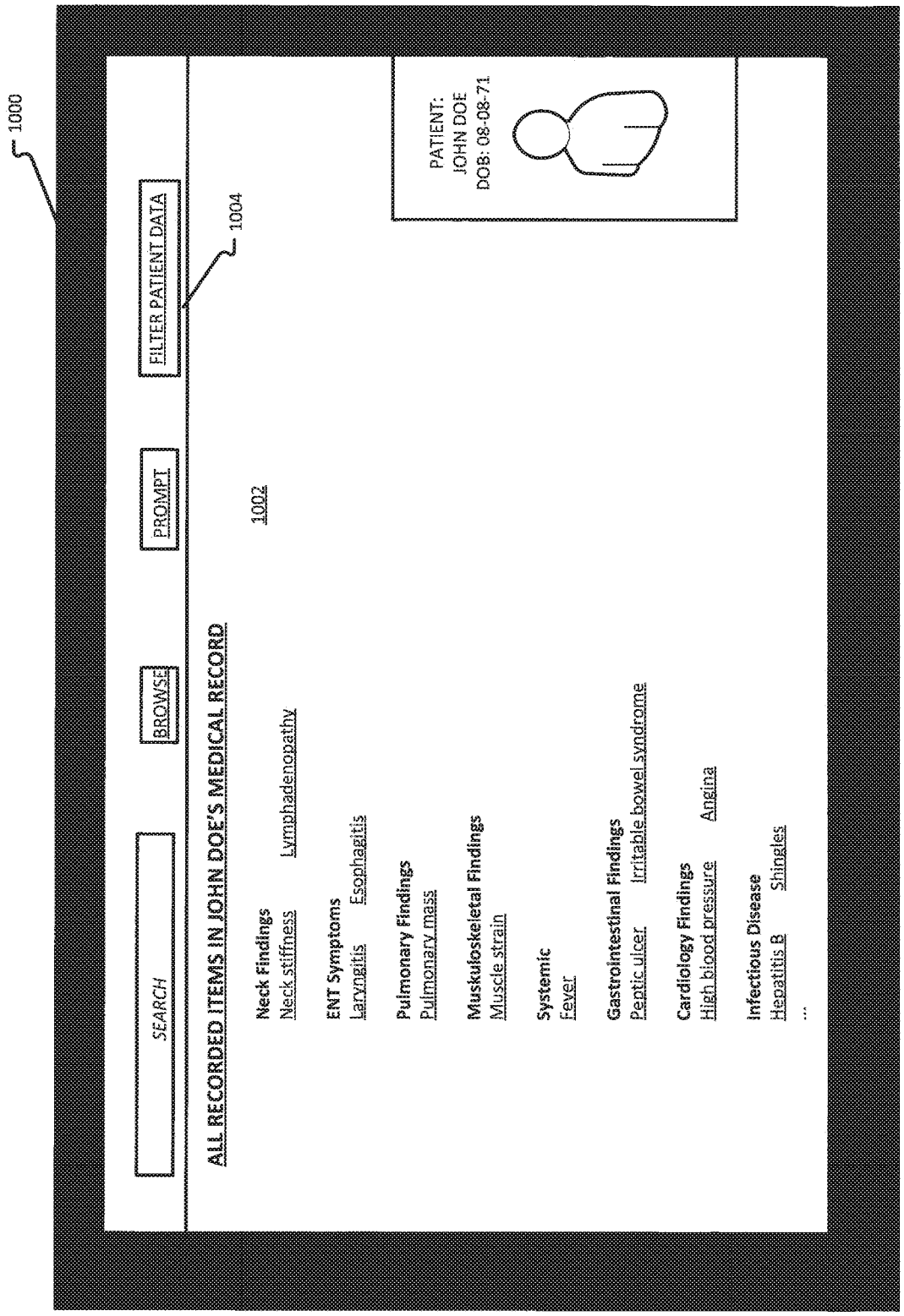
FIG. 12 is an exemplary embodiment of a caregiver user interface generated by the systems illustrated in FIGS. 1-3.

Referring now to FIG. 12, an exemplary embodiment of a graphical user interface (GUI) 1000 is shown. The GUI 1000 is an example of a patient's previously recorded medical record. In the example, the GUI 1000 includes the recorded data 1002 and a filtering option 1004.

The GUI 1000 is an example of what is presented to a caregiver when viewing a patient's entire medical record. It is understood that only a portion of John Doe's medical record is shown in the GUI 1000. The caregiver may select the filtering option 1004 to select one or more types of filters to filter findings 1002 recorded in the patient's medical record, as discussed above with reference to FIG. 6. The caregiver may wish to do so to identify past medical findings and conditions associated with the patient to determine a current health status of the patient.

Figure 13:
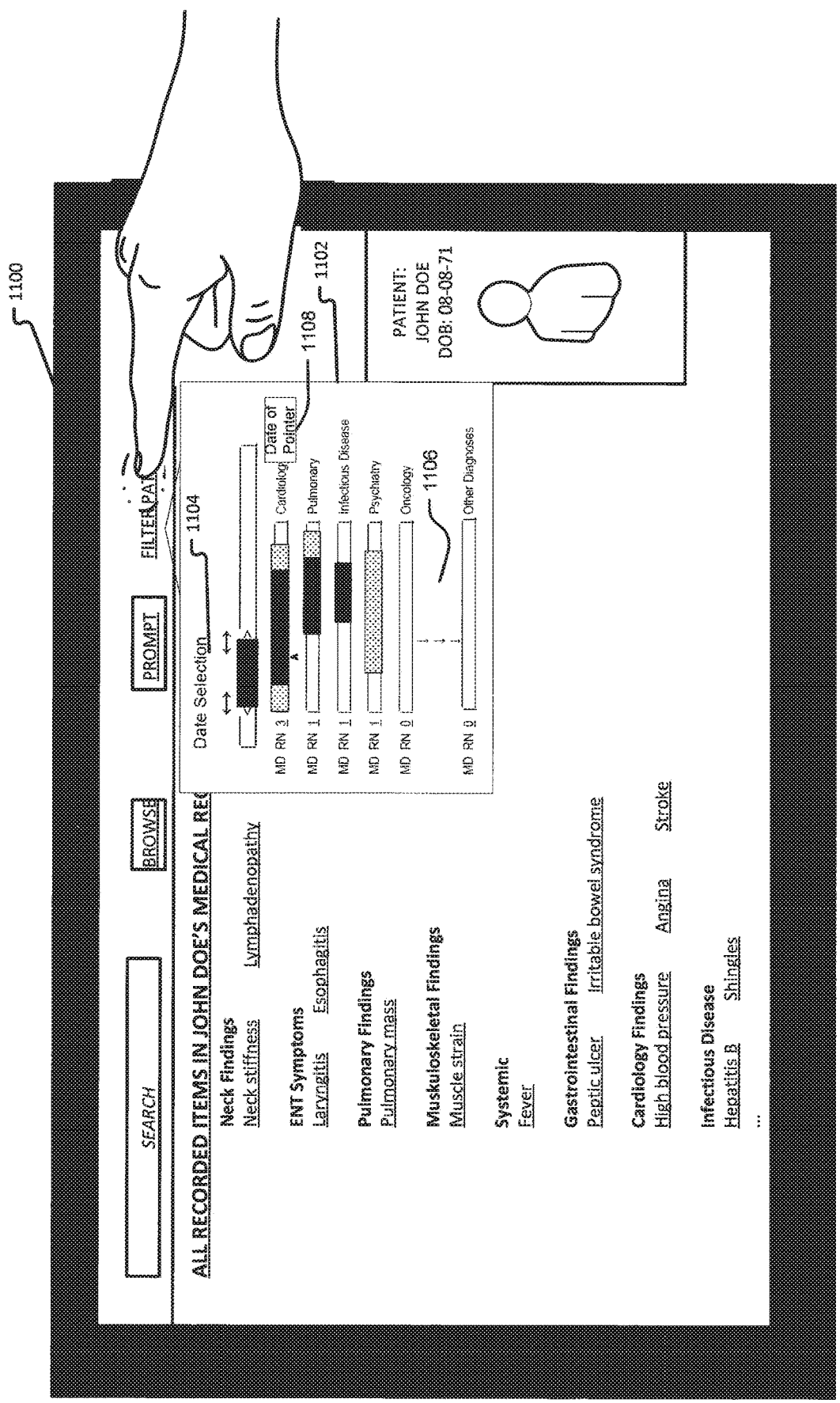
FIG. 13 is an exemplary embodiment of a caregiver user interface generated by the systems illustrated in FIGS. 1-3.

Now referring to FIG. 13, an exemplary embodiment of a GUI 1100 is shown. In general, the GUI 1100 is an example of a user interface and information shown to the caregiver after the caregiver has selected the filtering option 1004. The GUI 1100 includes a filtering box 1102. The filtering box 1102 includes a date selection filtering bar 1104, type filtering bar 1106, and a date indicator field 1108. In the example, the caregiver may select the filtering bars 1104, 1106 to narrow the listing of recorded medical findings to a more manageable listing of recorded items that are relevant to the present patient encounter.

In at least some embodiments, the filtering box 1102 includes only one of the date filtering bar 1104 or type filtering bar 1106. In the embodiment illustrated in FIG. 13, both kinds of filtering bars 1104, 1106 are present. The caregiver may utilize similar methods as described with respect to the touch screen and input in FIG. 8 to move, stretch, and/or shrink the bars 1104, 1106 to a desirable position. Alternative embodiments can include other types of interfaces for entering or setting parameters, such as spin dials and data fields, instead of slide bars.

The date selection filtering bar 1104 allows the caregiver to identify a time period during which medical findings were recorded in the patient medical record. Thus, by selecting a particular time frame, the listing of all medical findings may be filtered to only those items that were recorded during the selected time frame. In at least some embodiments, as the caregiver slides the bar 1104, the GUI 1100 indicates the time frame (e.g., the beginning date and the ending date) for the caregiver. The date filtering bar 1104 sets the time frame for filtering medical findings in a manner similar to other date slide bars disclosed herein.

In at least some embodiments, the caregiver may further select a number of a type of finding within the selected time period. For example, the caregiver may move, stretch, and/or shrink the bars 1106 to indicate a number of items desirable to be viewed in the particular category of items. In at least some embodiments, the bars 1106 are not presented to the caregiver until after a time period is selected on the bar 1104.

In at least some embodiments, colors may be utilized in the bars 1104, 1106 to indicate higher risk and/or higher complexity findings for a particular patient during the selected time period. As used herein, risk indicates a degree of severity with respect to the patient's survival for the listed entry. Complexity indicates a degree of complexity of the caregiver's procedure for handling/managing the listed entry. For example, in some instances, a white bar indicates that no entries were entered for a patient during a particular time period. In some examples, a yellow bar indicates that lower risk and/or lower complexity medical findings exist for a particular patient during the selected time period. In yet further embodiments, a red bar indicates that higher risk and/or higher complexity medical findings exist for a particular patient during the selected time period.

In various embodiments, the entire slide bar 1104, 1106 can be set to a particular color, or alternatively, only a portion of the slide bar 1104, 1106 corresponding to the medical finding causing the color to be displayed or corresponding to the date on which the medical findings causing the color to be displayed was recorded. Additionally, if the date selection bar 1104 is colored, the color reflects the most critical status of the findings from the filtered medical records. Alternatively, if a type slide bar 1106 is colored, it reflects the status of only the findings corresponding to the particular slide bar 1106 bearing the color.

In some examples, as the caregiver taps or hovers over certain portions of the type filtering bars 1106, the RMD filtering engine 204 identifies the medical finding corresponding to the point along the slide bar 1106 being actuated. GUI 1100 can then display the identified medical findings recorded in the patient medical record during that time period to provide the caregiver with some insight as to why a certain portion of the bars 1106 are a certain color. In other embodiments, a date box 1108 is presented to the side of the bars 1106 to indicate the exact date at which the pointer is located on the bars 1106.

In yet further embodiments, the date selection filtering bar 1104 is independent of the type filtering bars 1106. Thus, the caregiver may be presented with simply one of the bars 1104, 1106. In such embodiments, the type filtering bars 1106 do not depend on the time frame set by the date selection filtering bar 1104, and the filtered medical findings as set by the type filtering bar 1106 may include findings from the specified type from the patient's entire medical record or may include findings for a default time period, such as, for example, the last five years.

Figure 14:
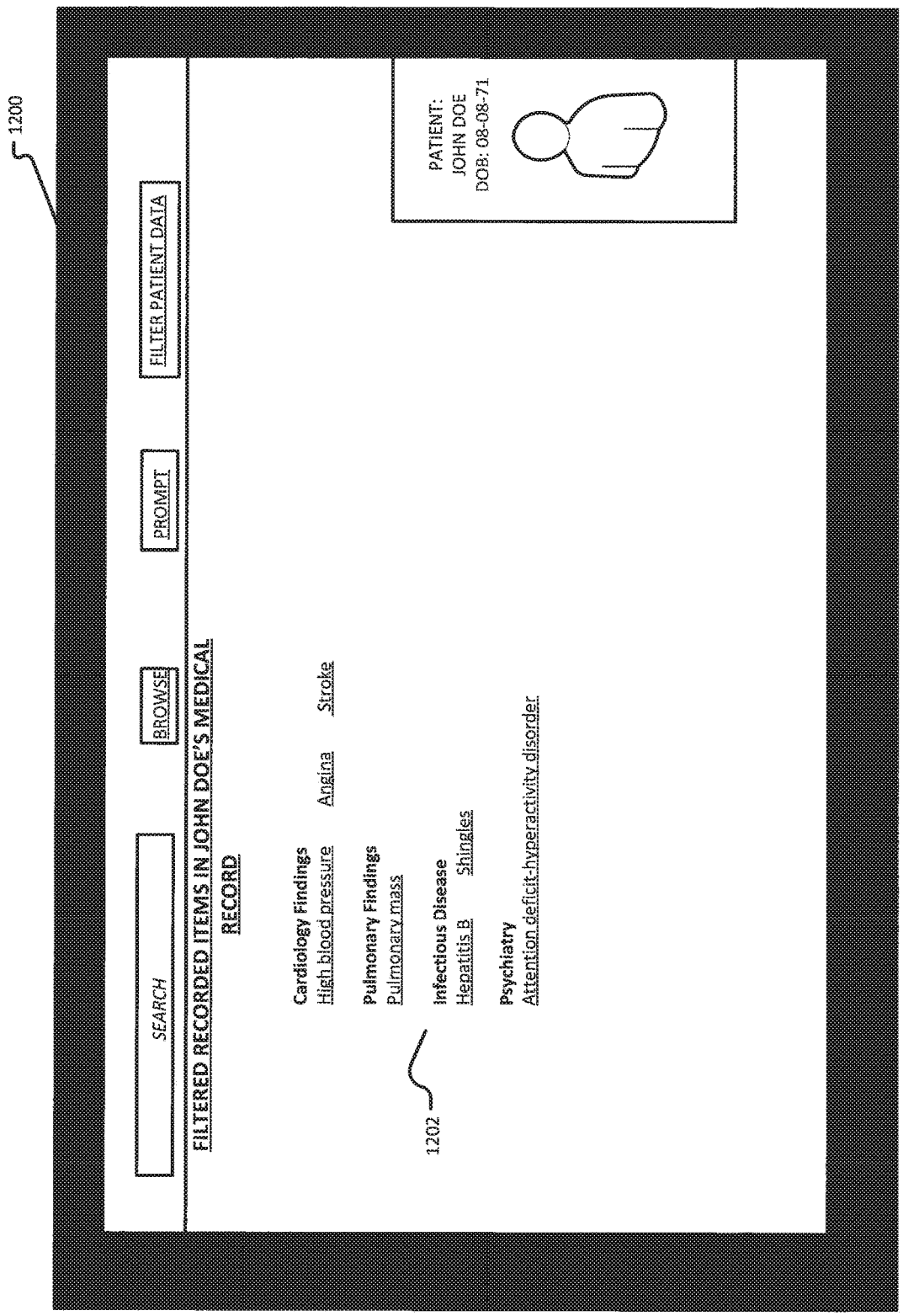
FIG. 14 is an exemplary embodiment of a caregiver user interface generated by the systems illustrated in FIGS. 1-3.

Now referring to FIG. 14, an exemplary embodiment of a GUI 1200 is shown. In general, the GUI 1200 is an example of the user interface and information presented to the caregiver after the caregiver has utilized one or both of the date selection filtering bar 1104 and the type filtering bars 1106 to set a filtered time frame and/or type. In the example, the GUI 1200 includes a filtered listing of medical findings 1202 from the patient's medical record.

The filtered listing of medical findings 1202 is an example of an output of one or both of the date selection engine 402 and the type filtering engine 404. In at least some embodiments, as shown, the filtered listing of medical findings 1202 is categorized based on the categories indicated in the type filtering bars 1106, as shown. In yet further embodiments, the GUI 1200 may indicate the caregiver selected time period indicated via the date selection filtering bar 1104. In at least some embodiments, one or more of the displayed medical findings can include a control or link to medical records of a particular patient encounter in which the displayed findings were recorded. The caregiver may select the control or link to learn more about the patient's encounter with the item. In yet further embodiments, selecting an item in the filtered listing of medical findings, allows the caregiver to view the entire patient record with respect to the selected item.

Figure 15:
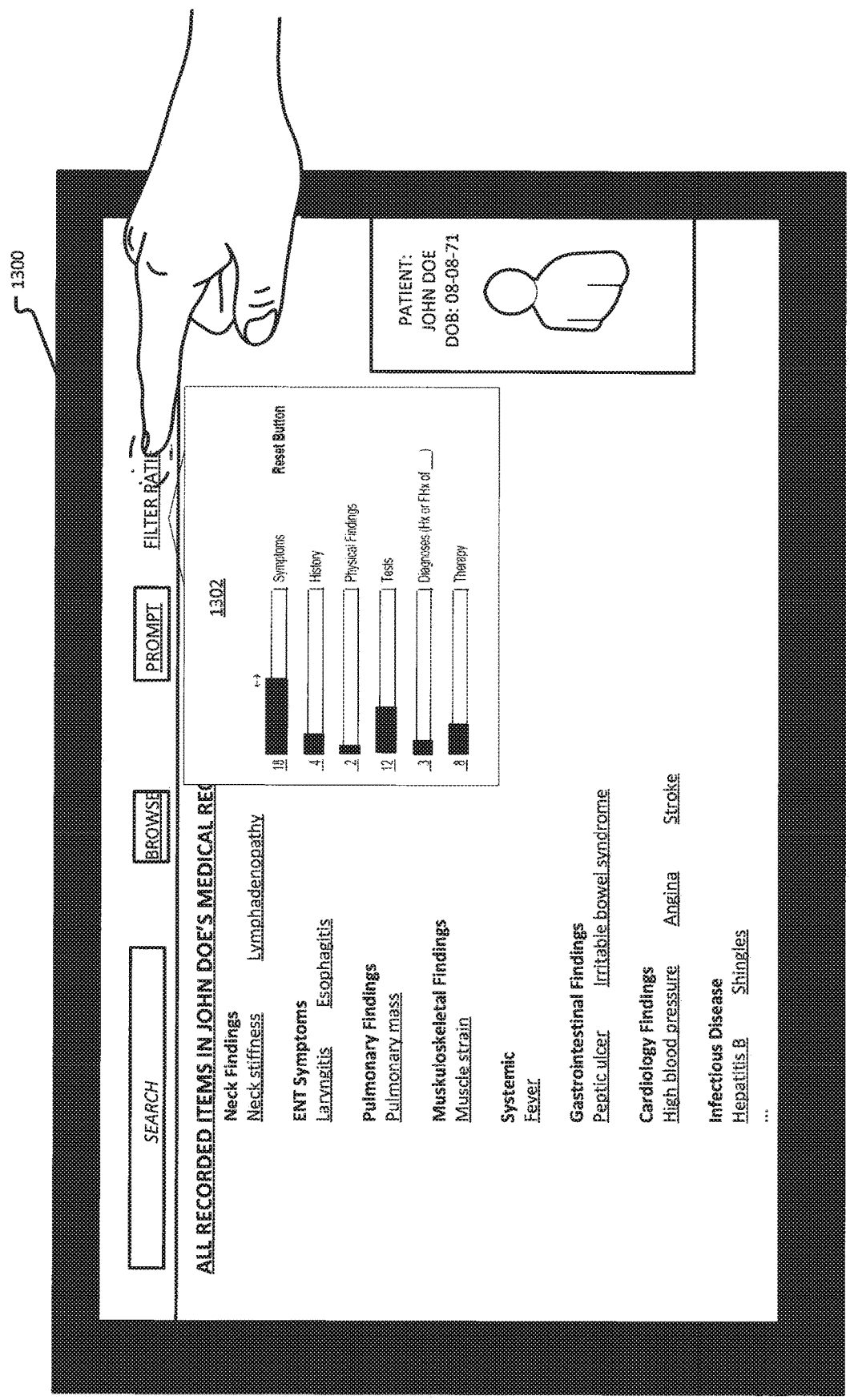
FIG. 15 is an exemplary embodiment of a caregiver user interface generated by the systems illustrated in FIGS. 1-3.

Now referring to FIG. 15, an exemplary embodiment of a GUI 1300 is shown. In general, the GUI 1300 is an example of the user interface and information shown to the caregiver after the caregiver has selected the filtering data option bar 1104. The GUI 1300 includes a filtering box 1302.

The filtering box 1302 allows the caregiver to filter the patient's medical history by form. For example, form may include, but is not limited to, symptoms, history, physical findings, test, therapy, and other medical findings. The caregiver may wish to review a particular form of medical findings from the patient's medical history.

Similar to other filtering boxes described herein, the filtering box 1302 includes slide bars or other data selection interfaces for setting the number of findings having each particular form to display. A number near the bars indicates the selected number of each form of a patient's medical findings selected by the caregiver. Alternative embodiments include a filter for screening dates that medical findings of a particular type were recorded in the patient's medical record.

Figure 16:
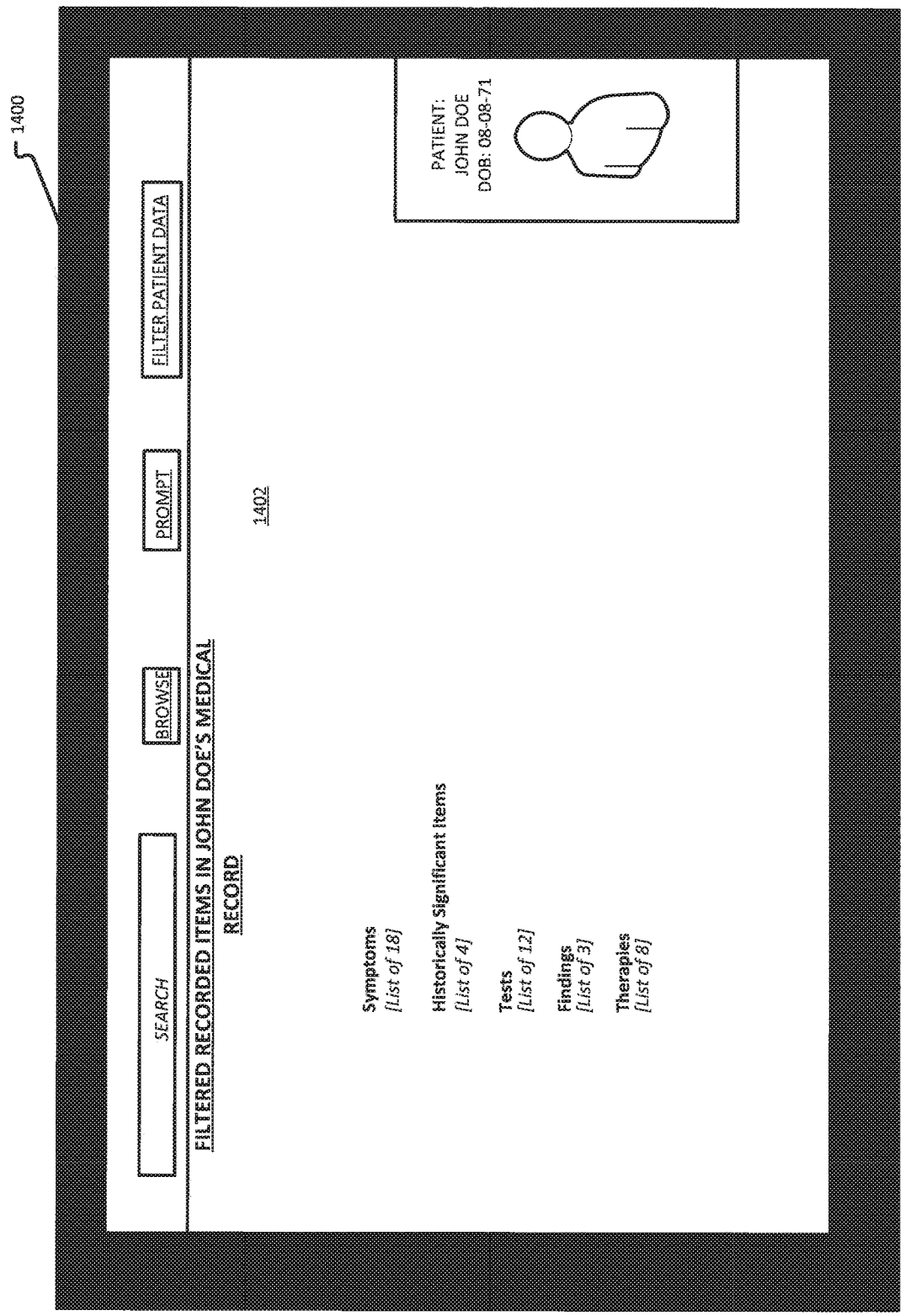
FIG. 16 is an exemplary embodiment of a caregiver user interface generated by the systems illustrated in FIGS. 1-3.

Now referring to FIG. 16, an exemplary embodiment of a GUI 1400 is shown. The GUI 1400 includes a filtered list of medical findings 1402. The filtered list of medical findings 1402 is an example of an output of the hierarchical filtering engine 406.

In at least some embodiments, such as the present example, the caregiver may desire to view a greater number of a particular form of medical findings than exists in the patient's medical record. In such situations, the hierarchical filtering engine 406 may access internal or external information located in the database 108 to identify and present medical findings or other information associated with the recorded medical findings in the patient's record. The caregiver may use underlining, highlighting, or some other indicia to differentiate between medical findings recorded in the patient's record and related medical findings. For example, as stated above, medical findings that appear in the patient's medical records are underlined and act as links that can redirect the caregiver to the exact entry in the patient medical record. Alternatively, the system 102 may highlight or color related medical findings differently to differentiate it from the medical findings in the patient's record.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A system comprising:
   a database encoded on a memory device, the database comprising medical findings related to a patient;

a computing device in data communication with the database, wherein the computing device is programmed to:

receive medical data;

determine findings in the database that are associated with the medical data;

generate a graphical user interface, the graphical user interface having one or more adjustable graphical control elements, at least one of the one or more adjustable graphical control elements corresponding to one category of medical findings, the adjustable graphical control element representing filter guidelines, the adjustable graphical control element defining a value in a range of values, the value defining a number of medical findings in the category of medical findings, the adjustable graphical control element having a color, the color representing a state of the medical findings;

present, on the graphical user interface, the number of medical findings, the number of findings displayed on the graphical user interface corresponding to the number of medical findings defined by the adjustable graphical control element;

receive, from the user, the filter guidelines via the one or more adjustable graphical control elements; and filter the findings based on user inputted guidelines.

2. The system of claim 1, wherein the adjustable graphical control elements are selected from the group consisting essentially of: a widget, a rotation widget, a slide bar, an icon, a button, a slider, a spinner, a dial, or combinations thereof.

3. The system of claim 1, wherein the filter guidelines comprise parameters defining a date range corresponding to the date that the filtered findings were recorded to present on the graphical user interface.

4. The system of claim 1, wherein the filter guidelines comprise parameters defining a percentage of the total number of filtered findings for selected medical specialties.

5. The system of claim 1, wherein the filter guidelines comprise parameters defining filtered findings to present on the graphical user interface according to a form of the filtered finding.

* * * * *